US009260503B2

(12) United States Patent
Hoeg-Jensen et al.

(10) Patent No.: US 9,260,503 B2
(45) Date of Patent: Feb. 16, 2016

(54) MULTI-SUBSTITUTED INSULINS

(75) Inventors: Thomas Hoeg-Jensen, Klampenborg (DK); Peter Madsen, Bagsvaerd (DK); Jane Spetzler, Broenshoej (DK); Tina Moeller Tagmose, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/126,215

(22) PCT Filed: Jun. 14, 2012

(86) PCT No.: PCT/EP2012/061284
§ 371 (c)(1),
(2), (4) Date: Mar. 21, 2014

(87) PCT Pub. No.: WO2012/171994
PCT Pub. Date: Dec. 20, 2012

(65) Prior Publication Data
US 2014/0228285 A1   Aug. 14, 2014

Related U.S. Application Data

(60) Provisional application No. 61/499,203, filed on Jun. 21, 2011.

(30) Foreign Application Priority Data

Jun. 15, 2011   (EP) ..................................... 11170009

(51) Int. Cl.
*C07K 14/62* (2006.01)
*C07K 1/107* (2006.01)

(52) U.S. Cl.
CPC ............. *C07K 14/622* (2013.01); *C07K 1/1077* (2013.01); *C07K 14/62* (2013.01)

(58) Field of Classification Search
CPC ............................... C07K 14/62; C07K 1/1077
See application file for complete search history.

(56) References Cited

U.S. PATENT DOCUMENTS

| | | | |
|---|---|---|---|
| 3,528,960 | A | 9/1970 | Haas |
| 3,864,325 | A | 2/1975 | Smyth |
| 3,868,356 | A | 2/1975 | Smyth |
| 3,869,437 | A | 3/1975 | Lindsay et al. |
| 5,905,140 | A | 5/1999 | Hansen |
| 6,531,448 | B1 | 3/2003 | Brader |
| 2006/0018874 | A1 | 1/2006 | Radhakrishnan et al. |
| 2013/0190232 | A1* | 7/2013 | Tagmose ............ A61K 38/1825 514/4.8 |

FOREIGN PATENT DOCUMENTS

| | | |
|---|---|---|
| JP | 1254699 A | 10/1989 |
| WO | 99/21578 A1 | 5/1999 |
| WO | 99/22754 A1 | 5/1999 |
| WO | 99/32116 A1 | 7/1999 |
| WO | 01/00675 A1 | 1/2001 |
| WO | 01/93837 A2 | 12/2001 |
| WO | 2005/016312 A1 | 2/2005 |
| WO | 2007/096431 A1 | 8/2007 |
| WO | 2008/013938 A2 | 1/2008 |
| WO | 2008/015099 A2 | 2/2008 |
| WO | 2008/145721 A2 | 12/2008 |
| WO | 2009/015456 A1 | 2/2009 |
| WO | 2009/022005 A1 | 2/2009 |
| WO | 2009/067636 A2 | 5/2009 |
| WO | WO 2009/115469 * | 9/2009 |
| WO | 2010/029159 A1 | 3/2010 |
| WO | 2010/080609 A1 | 7/2010 |

OTHER PUBLICATIONS

Asada et al. "Absorption Characteristics of Chemically Modified-Insulin Derivatives with Various Fatty Acids in the Small and Large Intestine," Journal of Pharmaceutical Sciences, Jun. 1995, vol. 84, pp. 682-687.*
Asada H et al., Stability of acyl derivatives of insulin in the small intestine: Relative importance of insulin association characteristics in aqueous solution, Pharmaceutical Research, 1994, vol. 11 (8), 1115-1120.
D. G. Lindsay et al., Acetoacetylation of insulin, The Biochemical Journal, 1969, vol. 115(3), 587-595.
D. G. Lindsay et al., The Acetylation of Insulin, Biochemical Journal, 1971, vol. 121, 737-745.
Ehrat M. et al., Synthesis and Spectroscopic Characterization of Insulin Derivatives Containing One or Two Poly (ethylene oxide) Chains at Specific Positions, Biopolymers, 1983, vol. 22, 569-573.
Friesen Heinz-Jurgen et al., Preparation and Application of Nalpha -B1, N epsilon-B29-bis(tert.-butyloxycarbonyl) insulin, Hoppe-Seyler's Z. Physiological Chemistry, 1978, vol. 359, 103-111.
Hashimoto M et al., Synthesis of palmitoyl derivatives of insulin and their biological activities, Pharmaceutical Research, 1989, vol. 6(2), 171-176.
Hashizume M et al., Improvement of large intestinal absorption of insulin by chemical modification with palmitic acid in rats, The Journal of pharmacy and pharmacology, 1992, vol. 44(7), 555-559.
Lindsay D.G. et al., Carbamyl- and methylthiocarbamylinsulins, Biochimica et Biophysica Acta (BBA)—Protein Structure, 1972, vol. 263 (3), 658-665.
Shozo Muranishi et al., Trials of lipid modification of peptide hormones for intestinal delivery, Journal of Controlled Release, 1992, vol. 19, Issues 1-3, 179-188.
Takashi Uchio et al., Site-specific insulin conjugates with enhanced stability and extended action profile, Advanced Drug Delivery Reviews, 1999, vol. 35, Issues 2-3, 289-306.
Ulla Ribel et al., Equivalent In Vivo Biological Activity of Insulin Analogues and Human Insulin Despite Different In Vitro Potencies, Diabetes, 1990, vol. 39, 1033-1039.
Yogish C Kudva et al., Ultra-long-acting insulins for a lifestyle-related pandemic, The Lancet, 2011, vol. 377(9769), 880-881.

* cited by examiner

*Primary Examiner* — Christina Bradley
(74) *Attorney, Agent, or Firm* — Jianjie Hu

(57) ABSTRACT

The present invention regards an insulin derivative comprising at least 2 albumin binding moieties, wherein said albumin binding moieties comprise fatty diacid substitutions and a method for preparing such an insulin derivative by acylation and/or reductive alkylation. The present invention also concern a pharmaceutical comprising such an insulin derivative.

15 Claims, No Drawings

MULTI-SUBSTITUTED INSULINS

CROSS-REFERENCE TO RELATED APPLICATIONS

This application is a 35 U.S.C. §371 National Stage application of International Application PCT/EP2012/061284 (WO2012/171994), filed Jun. 14, 2012, which claimed priority of European Patent Application 11170009.2, filed Jun. 15, 2011; this application claims priority under 35 U.S.C. §119 of U.S. Provisional Application 61/499,203; filed Jun. 21, 2011.

TECHNICAL FIELD

The present invention relates to novel insulin derivatives which are useful in the treatment of diabetes and related aspects.

BACKGROUND

In mammals, insulin lowers blood glucose and is used for treatment of diabetes type 1 and type 2, with the goal of adjusting blood glucose towards healthy levels. In healthy persons, blood glucose levels are regulated close to 5 mM during the fasting state, whereas values up towards 10 mM can occur for a few hours after a meal. Blood glucose levels are influenced by many factors such as timing and character of meals and insulin administrations, exercise, infections and more. Blood glucose can fluctuate widely and unpredictably in diabetes patients and can fluctuate in one patient in the range 1-30 mM.

Diabetes patients benefit from a constant supply of basal insulin drug, because native insulin is quickly cleared from the body. In order to limit the number of injections required for maintaining basal insulin levels, insulin has been engineered with various prolongation principles, such as crystallizations or chemical derivatisations.

Reversible binding to circulating proteins such as serum albumin can also be a factor prolonging the in vivo activity of drugs. Albumin binding as a protraction principle has been exploited for insulin and other peptides by conjugation of the drug with fatty acids, fatty diacids or related compounds, optionally incorporated via various linkers.

Low affinity insulin analogs have been shown to give rise to an equivalent total effect on glucose utilization as high affinity analogs in euglycemic glucose-clamp studies in pigs, suggesting that the insulin biological activity can be similar for both low- and high-affinity analogues. However the low affinity analogs exerted their effect over a longer time period when compared to the high affinity analogues (See e.g. Ribel, U., et. al. Equivalent in vivo biological activity of insulin analogues and human insulin despite different in vitro potencies. *Diabetes* 39, 1033-1039 (1990), abstract attached).

WO1999/032116 and WO1999/021578 regard fatty acid-acylated insulins, WO1999/022754, WO1999/032116, WO1999/021578, JP1254699 administering a fatty acid di- and triacylated insulin or insulin analogue by inhalation, U.S. Pat. No. 3,868,356 concerns acylation of insulins with dicarboxylic acid functional derivatives, e.g. anhydrides.

There is still a need for basal insulin drugs with a prolonged in vivo activity.

SUMMARY

The present invention regards an insulin derivative comprising two or more substitutions, each comprising a fatty diacid substitution, the insulin derivative optionally comprises a linker between the insulin and the fatty acid substitution.

The present invention also regards a method for preparing such an insulin derivative or a pharmaceutical salt thereof by acylation and/or reductive alkylation of an insulin.

The present invention regards an insulin derivative for the treatment of diabetes or related aspects and may thus also be used as a medicament.

DESCRIPTION

The present invention regards an insulin, substituted with at least two albumin binding moieties, each comprising a protracting moiety, which more specifically is a fatty diacid substitution. Optionally the albumin binding moiety further comprises various linkers. The derivatisation of an insulin according to this invention is achieved by acylation and/or reductive alkylation, obtaining an increased albumin affinity and in vivo circulation times of the resulting insulin derivative relative to native human insulin.

The present invention also provides a method for reductive alkylation of the B1 residue (e.g. the N-terminal of the B-chain of the insulin).

The present invention also provides a method for reductive alkylation of the A1 residue (e.g. the N-terminal of the A-chain of the insulin).

The object of this invention is to overcome or ameliorate at least one of the disadvantages of the prior art, or to provide a useful alternative.

The invention may also solve further problems that will be apparent from the disclosure of the exemplary embodiments.

It has been found, that substitution of insulins or insulin analogues with at least two fatty diacids enables insulin binding to human serum albumin and prolongs the in vivo insulin supply, retaining IR-binding properties. This is favourable, since substitutions according to this invention are also possible on insulin analogues that have only very few (e.g. 2-6) mutations and thus this invention provides the option of prolonging the insulin in vivo supply of insulin and maintaining an insulin backbone that is very similar to the native human insulin.

In one aspect of the present invention the affinity of insulin derivatives substituted with at least two fatty diacids to albumin is increased when compared to single substituted insulin derivatives.

In one aspect of the present invention the prolongation effect is increased when compared to single substituted insulin derivatives.

The insulin derivatives of this invention are long-acting, and in one aspect they show increased tendency to oligomerisation in the subcutaneous depot, enabling slow diffusion to the circulation.

In one aspect the affinity of an insulin derivative according to the present invention to albumin is elevated with increasing fatty diacid chain length.

In one aspect the affinity of an insulin derivative according to the present invention to albumin is elevated with increasing fatty diacid chain up to 22 carbon atoms.

In one aspect the insulin derivative is maintained overall hydrophilic with increasing fatty diacid chain up to 22 carbon atoms.

In one aspect the prolongation effect of at least two albumin binding moieties according to this invention is elevated with increasing fatty diacid chain length.

In one aspect the prolongation effect of at least two albumin binding moieties according to this invention is elevated with increasing fatty diacid chain up to 22 carbon atoms.

In one embodiment an insulin derivative according to the present invention comprises at fatty diacid substitution consisting of up to 22 carbon atoms. In one embodiment an insulin derivative according to the present invention comprises at fatty diacid substitution consisting of 10-22 carbon atoms. In one embodiment an insulin derivative according to the present invention comprises at fatty diacid substitution consisting of 10-20 carbon atoms. In one embodiment an insulin derivative according to the present invention comprises at fatty diacid substitution consisting of 10-18 carbon atoms. In one embodiment an insulin derivative according to the present invention comprises at fatty diacid substitution consisting of 10-16 carbon atoms. In one embodiment an insulin derivative according to the present invention comprises at fatty diacid substitution consisting of 10-14 carbon atoms. In one embodiment an insulin derivative according to the present invention comprises at fatty diacid substitution consisting of 12-20 carbon atoms. In one embodiment an insulin derivative according to the present invention comprises at fatty diacid substitution consisting of 12-18 carbon atoms. In one embodiment an insulin derivative according to the present invention comprises at fatty diacid substitution consisting of 12-16 carbon atoms. In one embodiment an insulin derivative according to the present invention comprises at fatty diacid substitution consisting of 12-14 carbon atoms. In one embodiment an insulin derivative according to the present invention comprises at fatty diacid substitution consisting of 14-20 carbon atoms. In one embodiment an insulin derivative according to the present invention comprises at fatty diacid substitution consisting of 14-18 carbon atoms. In one embodiment an insulin derivative according to the present invention comprises at fatty diacid substitution consisting of 14-16 carbon atoms. In one embodiment an insulin derivative according to the present invention comprises at fatty diacid substitution consisting of 10, 11, 12, 13, 14, 15, 16, 17, 18, 19 or 20 carbon atoms. In one embodiment an insulin derivative according to the present invention comprises at fatty diacid substitution consisting of 14, 15, 16, 17, 18, 19 or 20 carbon atoms. In one embodiment an insulin derivative according to the present invention comprises at fatty diacid substitution consisting of 16, 17, 18, 19 or 20 carbon atoms.

In one embodiment of the present invention an insulin derivative comprises at least 2 albumin binding moieties, wherein said albumin binding moieties comprise fatty diacid substitutions and wherein one carboxy group from each of said fatty diacid substitutions are attached, optionally via a linker, to an insulin.

In one embodiment of the present invention an insulin derivative comprises at least 3 albumin binding moieties, wherein said albumin binding moieties comprise fatty diacid substitutions and wherein one carboxy group from each of said fatty diacid substitutions are attached, optionally via a linker, to an insulin.

In one embodiment of the present invention an insulin derivative comprises 2 or 3 albumin binding moieties, wherein said albumin binding moieties comprise fatty diacid substitutions and wherein one carboxy group from each of said fatty diacid substitutions are attached, optionally via a linker, to an insulin.

In one embodiment of the present invention an insulin derivative comprises 2 albumin binding moieties, wherein said albumin binding moieties comprise fatty diacid substitutions and wherein one carboxy group from each of said fatty diacid substitutions are attached, optionally via a linker, to an insulin.

In one embodiment of the present invention an insulin derivative comprises 2 albumin binding moieties, wherein said albumin binding moieties comprise fatty diacid substitutions and wherein one carboxy group from each of said fatty diacid substitutions are attached, optionally via a linker, to amino acid residues in an insulin.

In one embodiment of the present invention an insulin derivative comprises 2 albumin binding moieties, wherein said albumin binding moieties comprise fatty diacid substitutions and wherein one carboxy group from each of said fatty diacid substitutions are attached, optionally via a linker, to amino acid residues in an insulin located in any of the following positions: A22, B29 or the N-terminal amino acid residue of the A chain of an insulin and/or the N-terminal amino acid residue of the B chain of an insulin.

In one embodiment of the present invention an insulin derivative comprises 3 albumin binding moieties, wherein said albumin binding moieties comprise fatty diacid substitutions and wherein one carboxy group from each of said fatty diacid substitutions are attached, optionally via a linker, to an insulin.

In one embodiment of the present invention an insulin derivative comprises 3 albumin binding moieties, wherein said albumin binding moieties comprise fatty diacid substitutions and wherein one carboxy group from each of said fatty diacid substitutions are attached, optionally via a linker, to amino acid residues in an insulin.

In one embodiment of the present invention an insulin derivative comprises 3 albumin binding moieties, wherein said albumin binding moieties comprise fatty diacid substitutions and wherein one carboxy group from each of said fatty diacid substitutions are attached, optionally via a linker, to amino acid residues in an insulin located in any of the following positions: A22, B29, the N-terminal amino acid residue of the A chain of an insulin and/or the N-terminal amino acid residue of the B chain of an insulin.

In one embodiment of the present invention an insulin derivative is represented by the general formula Chem 1:

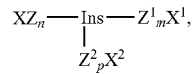

Chem. 1 in which Ins represents an insulin comprising a B29 lysine or B29 arginine residue and/or a A22 lysine residue, X, $X^1$ and $X^2$ is a fatty diacid substitution and $X^2$ is optional, Z, $Z^1$ and $Z^2$ is a linker between Ins and X, $X^1$ and $X^2$, respectively and n, m and p is zero or one.

In one embodiment of the present invention an insulin derivative is represented by the general formula Chem 1, in which Ins represents an insulin comprising a B29 lysine or B29 arginine residue and/or a A22 lysine residue, X, $X^1$ and $X^2$ is a fatty diacid substitution and respectively located in a position selected from the group consisting of: B29 lysine, A22 lysine, N-terminal of the A chain, N-terminal of the B-chain, Z, $Z^1$ and $Z^2$ is a linker between Ins and X, $X^1$ and $X^2$, respectively and n, m and p is zero or one.

In one embodiment of the present invention an insulin derivative is represented by the general formula Chem. 2:

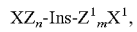

Chem 2 in which Ins represents an insulin comprising a B29 lysine or B29 arginine residue and/or a A22 lysine residue, X and $X^1$ is a fatty diacid substitution, Z and $Z^1$ is a linker between Ins and X and $X^1$ respectively, and n and m is zero or one.

In one embodiment of the present invention an insulin derivative is represented by the general formula Chem. 2, in which Ins represents an insulin comprising a B29 lysine or B29 arginine residue and/or a A22 lysine residue, X and $X^1$ is a fatty diacid substitution and respectively located in a position selected from the group consisting of: B29 lysine, A22 lysine, N-terminal of the A chain, N-terminal of the B-chain, Z and $Z^1$ is a linker between Ins and X and $X^1$ respectively, and n and m is zero or one.

When used herein "Z, $Z^1$ and $Z^2$ is a linker between Ins and X, $X^1$ and $X^2$, respectively" or "Z and $Z^1$ is a linker between Ins and X and $X^1$ respectively" means that Z, $Z^1$ or $Z^2$ is a linker between the amino acid in the insulin (Ins) and the respective protraction moiety X, $X^1$ or $X^2$. More specifically this means, that Z is a linker between the insulin (Ins) and the protracting moiety X, $Z^1$ is a linker between the insulin (Ins) and the protracting moiety $X^1$ and $Z^2$ is a linker between the insulin (Ins) and the protracting moiety $X^2$.

The letters n, m and p of Chem. 1 and Chem. 2 independently represent the number of linkers (Z, $Z^1$ and $Z^2$, respectively) represented in the insulin derivative and n, m and p is zero or one. More specifically this means that when n is zero, no linker is present between the insulin (Ins) and the protraction moiety (X) in Chem. 1 or Chem. 2, when m is zero, no linker is present between the insulin (Ins) and the protraction moiety ($X^1$) in Chem. 1 or Chem. 2 an when p is zero, no linker is present between the insulin (Ins) and the protraction moiety ($X^2$) in Chem. 1, when n is one, one linker is present between the insulin (Ins) and the protraction moiety (X) in Chem. 1 or Chem. 2, when m is one, one linker is present between the insulin (Ins) and the protraction moiety ($X^1$) in Chem. 1 or Chem. 2 an when p is one, one linker is present between the insulin (Ins) and the protraction moiety ($X^2$) in Chem. 1.

The albumin binding moiety (e.g. $Z_nX$ in formula Chem. 1 and Chem. 2), the protracting moiety (e.g. X in formula Chem. 1 and Chem. 2) or the linker (e.g. Z in formula Chem. 1 and Chem. 2) may be covalently attached to a lysine residue or the N-terminal of the A and/or B chain of the insulin by acylation and/or reductive alkylation.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modifications relative to human insulin.

Modifications in the insulin molecule are denoted stating the chain (A or B), the position, and the one or three letter code for the amino acid residue substituting the native amino acid residue.

In one embodiment an insulin derivative according to this invention comprises at least 2 albumin binding moieties.

In one embodiment an albumin binding moiety (e.g. $Z_nX$ Chem. 1) of an insulin derivative according to the present invention comprises a protracting moiety, which may also be designated fatty diacid substitution (e.g. X in Chem. 1).

In one embodiment each albumin binding moiety of an insulin derivative according to the present invention comprises a protracting moiety and optionally a linker (e.g. $Z_n$ in Chem. 1, wherein n is one).

In one embodiment, an activated ester of the albumin binding moiety, preferably comprising a protracting moiety and a linker, is covalently linked to an amino group of a lysine residue, preferably the epsilon amino group thereof, under formation of an amide bond (this process being referred to as acylation).

In one embodiment, an activated ester of the albumin binding moiety (e.g. $Z_nX$, Chem. 1), preferably comprising a protracting moiety (e.g. X, Chem. 1) and a linker (e.g. $Z_n$ wherein n is one, Chem. 1), is covalently linked to an amino group of a lysine residue and/or an amino acid residue in the N-terminal of the A- or B-chain, preferably the epsilon amino group thereof, under formation of an amide bond (this process being referred to as acylation).

In one embodiment, an aldehyde derivative of the albumin binding moiety, preferably comprising a protracting moiety and a linker, is covalently linked by reductive alkylation to the alpha-amino group in the N-terminal of the A-chain or the alpha-amino group in the N-terminal of the B-chain or aldehyde derivatives are reductively alkylated at an N-terminal amino acid residue at A-chain and/or the B-chain.

In one embodiment, an aldehyde derivative of the albumin binding moiety, preferably comprising a protracting moiety and a linker, is covalently linked by reductive alkylation to a lysine residue, preferably the epsilon-amino group thereof.

In one embodiment an insulin according to the present invention comprises an arginine residue in position B29 and is substituted with an albumin binding moiety at the A22 lysine and not at the B29 position.

In one embodiment an insulin derivative according to this invention is desired to comprise one albumin binding moiety at the A22 position, one albumin binding moiety at another amino acid positions in the insulin and no albumin binding moiety at the B29 position, the insulin subject to substitution comprises an arginine residue in the B29 position.

In one embodiment an insulin derivative according to this invention is desired to comprise one albumin binding moiety at the A22 position, and one albumin binding moiety at an other amino acid positions of the insulin, such as the B29 position of the insulin, the insulin subject to substitution may comprise a lysine residue in the B29 position.

In one embodiment an insulin according to the present invention is substituted with an albumin binding moiety at the A22 lysine and the B29 lysine.

In one embodiment, each albumin binding moiety (e.g. $Z_nX$, Chem. 1) comprises a protracting moiety (e.g. X) independently selected from Chem. 3, and Chem. 4:

HOOC—(CH$_2$)$_x$—CO—*  Chem. 3

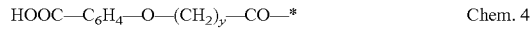

HOOC—C$_6$H$_4$—O—(CH$_2$)$_y$—CO—*  Chem. 4 in which x is an integer in the range of 10-20, y is an integer in the range of 6-14.

In one embodiment X of Chem. 1 or Chem. 2 is selected from Chem. 3, and Chem. 4:

HOOC—(CH$_2$)$_x$—CO—*  Chem. 3

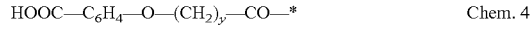

HOOC—C$_6$H$_4$—O—(CH$_2$)$_y$—CO—*  Chem. 4 in which x is an integer in the range of 10-20, y is an integer in the range of 6-14.

In one embodiment $X^1$ of Chem. 1 or Chem. 2 is selected from Chem. 3, and Chem. 4:

HOOC—(CH$_2$)$_x$—CO—*  Chem. 3

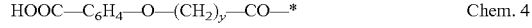

HOOC—C$_6$H$_4$—O—(CH$_2$)$_y$—CO—*  Chem. 4 in which x is an integer in the range of 10-20, y is an integer in the range of 6-14.

In one embodiment $X^2$ of Chem. 2 is selected from Chem. 3, and Chem. 4:

HOOC—(CH$_2$)$_x$—CO—*    Chem. 3

HOOC—C$_6$H$_4$—O—(CH$_2$)$_y$—CO—*    Chem. 4 in which s is an integer in the range of 10-20, t is an integer in the range of 6-14.

In one embodiment X, X$^1$ and X$^2$ of Chem. 1 or Chem. 2 are independently selected from Chem. 3, and Chem. 4:

HOOC—(CH$_2$)$_x$—CO—*    Chem. 3

HOOC—C$_6$H$_4$—O—(CH$_2$)$_y$—CO—*    Chem. 4 in which x is an integer in the range of 10-20, y is an integer in the range of 6-14.

In one embodiment, *—(CH$_2$)$_x$—* of Chem. 3 refers to straight or branched, preferably straight, alkylene in which x is an integer in the range of 10-20.

In another embodiment, *—(CH$_2$)$_y$—* of Chem. 4 refers to straight or branched, preferably straight, alkylene in which y is an integer in the range of 6-14.

In one embodiment, *—(CH$_2$)$_x$—* of Chem. 3 refers to straight or branched, preferably straight, alkylene in which x is an integer in the range of 12-20.

In another embodiment, *—(CH$_2$)$_y$—* of Chem. 4 refers to straight or branched, preferably straight, alkylene in which y is an integer in the range of 6-12.

In one embodiment, *—(CH$_2$)$_x$—* of Chem. 3 refers to straight or branched, preferably straight, alkylene in which x is an integer in the range of 14-20.

In another embodiment, *—(CH$_2$)$_y$—* of Chem. 4 refers to straight or branched, preferably straight, alkylene in which y is an integer in the range of 6-10.

In one embodiment, *—(CH$_2$)$_x$—* of Chem. 3 refers to straight or branched, preferably straight, alkylene in which x is an integer in the range of 14-16.

In another embodiment, *—(CH$_2$)$_y$—* of Chem. 4 refers to straight or branched, preferably straight, alkylene in which y is an integer in the range of 6-8.

In one embodiment, *—(CH$_2$)$_x$—* of Chem. 3 refers to straight or branched, preferably straight, alkylene in which x is an integer in the range of 12-18.

In another embodiment, *—(CH$_2$)$_y$—* of Chem. 4 refers to straight or branched, preferably straight, alkylene in which y is an integer in the range of 8-10.

In one embodiment, *—(CH$_2$)$_x$—* of Chem. 3 refers to straight or branched, preferably straight, alkylene in which x is an integer in the range of 14-18.

In another embodiment, *—(CH$_2$)$_y$—* of Chem. 4 refers to straight or branched, preferably straight, alkylene in which y is an integer in the range of 8-12.

In one embodiment, *—(CH$_2$)$_x$—* of Chem. 3 refers to straight or branched, preferably straight, alkylene in which x is an integer in the range of 10-16.

In another embodiment, *—(CH$_2$)$_y$—* of Chem. 4 refers to straight or branched, preferably straight, alkylene in which y is an integer in the range of 8-14.

In one embodiment, *—(CH$_2$)$_x$—* of Chem. 3 refers to straight or branched, preferably straight, alkylene in which x is an integer and selected from the group consisting of 12, 14, 16, 18 and 20.

In another embodiment, *—(CH$_2$)$_y$—* Chem. 4 refers to straight or branched, preferably straight, alkylene in which y is an integer and selected from the group consisting of 6, 8, 10, 12 and 14.

In one embodiment, *—(CH$_2$)$_x$—* of Chem. 3 refers to straight or branched, preferably straight, alkylene in which x is an integer and selected from the group consisting of 14, 16, 18 and 20.

In another embodiment, *—(CH$_2$)$_y$—* Chem. 4 refers to straight or branched, preferably straight, alkylene in which y is an integer and selected from the group consisting of 8, 10 and 12.

In one embodiment one of the acid groups of the fatty diacid forms an amide bond with the epsilon amino group of a lysine residue in said insulin, preferably via a linker.

The term "insulin subject to substitution" when used herein, means the insulin that is treated by the method provided herein and thus an insulin which is substituted with an albumin binding moiety, resulting in an insulin derivative according to this invention.

The term "fatty diacid" refers to fatty acids with an additional carboxylic acid group in the omega position. Thus, fatty diacids are dicarboxylic acids.

The nomenclature is as is usual in the art, for example in the above formulas *—COOH as well as HOOC—* refers to carboxy; *—C$_6$H$_4$—* to phenylene; *—CO—*, as well as *—OC—*, to carbonyl (O=C<**).

In particular embodiments, the aromatics, such as the phenoxy, and the phenylene radicals, may be, independently, ortho, meta, or para.

In one embodiment an insulin derivative according to this invention comprises at least 2 albumin binding moieties, each albumin binding moiety comprises a protracting moiety selected from Chem. 3, or 4.

In one embodiment an insulin derivative according to this invention comprises at least 2 albumin binding moieties, each albumin binding moiety comprises a protracting moiety selected from Chem. 3, or 4 and the albumin binding moiety optionally further comprises a linker, wherein each linker comprises one ore more linker element of formula Chem. 5, Chem. 6, Chem. 7, Chem. 8, Chem. 9, Chem. 10, and/or Chem. 11.

In one embodiment an insulin derivative according to this invention comprises at least 2 albumin binding moieties, each albumin binding moiety comprises a protracting moiety selected from Chem. 3, or 4 and the albumin binding moiety further comprises a linker (which may be designated Z).

In one embodiment a linker comprises one or more linker elements of formula Chem. 5, Chem. 6, Chem. 7, Chem. 8, Chem. 9, Chem. 10, and/or Chem. 11.

In one embodiment a linker element according to this invention may be designated e.

In one embodiment a linker (Z) comprises two linker elements, which may be designated $e_1$-$e_2$, indicating the arrangement relative to each other, e.g. linker element $e_1$ is attached to linker element $e_2$.

In one embodiment a linker (Z) comprises three linker elements, which may be designated $e_1$-$e_2$-$e_3$, indicating the arrangement relative to each other, e.g. linker element $e_1$ is attached to linker element $e_2$ and linker element $e_2$ is attached to linker element $e_1$ and linker element $e_3$.

In one embodiment a linker (Z) comprises four linker elements, which may be designated $e_1$-$e_2$-$e_3$-$e_4$, indicating the arrangement relative to each other, e.g. linker element $e_1$ is attached to linker element $e_2$ and linker element $e_2$ is attached to linker element $e_1$ and linker element $e_3$ and linker element $e_3$ is attached to linker element $e_4$.

In one embodiment a linker (Z) comprises four linker elements, which may be designated $e_1$-$e_2$-$e_3$-$e_4$-$e_5$, indicating the arrangement relative to each other, e.g. linker element $e_1$ is attached to linker element $e_2$ and linker element $e_2$ is attached to linker element $e_1$ and linker element $e_3$, linker element $e_3$ is attached to linker element $e_4$ and $e_4$ is attached to linker element $e_5$.

In one embodiment a linker (Z) comprises four linker elements, which may be designated $e_1$-$e_2$-$e_3$-$e_4$-$e_5$-$e_6$, indicating the arrangement relative to each other, e.g. linker element $e_1$ is attached to linker element $e_2$ and linker element $e_2$ is attached to linker element $e_1$ and linker element $e_3$, linker element $e_3$ is attached to linker element $e_4$, $e_4$ is attached to linker element $e_5$ and $e_5$ is attached to linker element $e_6$.

In one embodiment a linker element of a linker according to the present invention, designated with the highest number (e.g. $e_4$ in the linker $e_1$-$e_2$-$e_3$-$e_4$ or $e_3$ in the linker $e_1$-$e_2$-$e_3$) is attached to a protracting moiety (i.e. a fatty diacid).

A linker of the derivative of the invention may comprise the following first linker element:

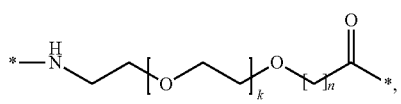

Chem 5 wherein k is an integer in the range of 1-5, and n is an integer in the range of 1-5.

In a particular embodiment, when k=1 and n=1, this linker element may be designated OEG, or a di-radical of 8-amino-3,6-dioxaoctanic acid, and/or it may be represented by the following formula:

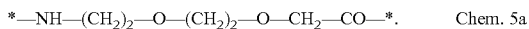  Chem. 5a

In one embodiment, each linker of the derivative of the invention further comprise, independently or in combination with one or more other linker element, a second linker element, preferably a Glu di-radical, such as Chem. 6 and/or Chem. 7:

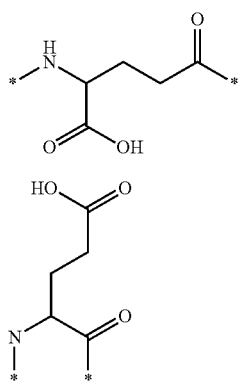

Chem. 6

Chem. 7 wherein the Glu di-radical may be included p times, where p is an integer in the range of 1-3.

Chem. 6 may also be referred to as gamma-Glu, or briefly g-Glu, due to the fact that it is the gamma carboxy group of the amino acid glutamic acid which is here used for connection to another linker element, or to the epsilon-amino group of lysine. The other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem. 7 may also be referred to as alpha-Glu, or briefly aGlu, or simply Glu, due to the fact that it is the alpha carboxy group of the amino acid glutamic acid which is here used for connection to another linker element, or to the epsilon-amino group of lysine or to the N-terminal of the A-chain or B-chain.

The above structures of Chem. 6 and Chem. 7 cover the L-form, as well as the D-form of Glu. The L-form may be designated gamma-L-Glu or gLGlu, whereas the D-form may be designated gamma-D-Glu or gDGlu. In particular embodiments, Chem. 6 and/or Chem. 7 is/are, independently, a) in the L-form, or b) in the D-form.

In one embodiment, each linker of the derivative of the invention further comprise, independently or in combination with one or more other linker element, a second linker element, preferably a Asp di-radical, such as Chem. 8 and/or Chem. 9:

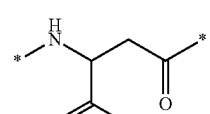

Chem. 8

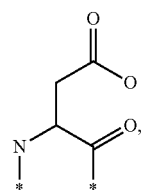

Chem. 9 wherein the Asp di-radical may be included p times, where p is an integer in the range of 1-3.

Chem. 8 may also be referred to as beta-Asp, or briefly bAsp, due to the fact that it is the gamma carboxy group of the amino acid aspartic acid which is here used for connection to another linker element, or to the epsilon-amino group of lysine or to the N-terminal of the A-chain or B-chain. The other linker element may, for example, be another Asp residue, or an OEG molecule. The amino group of Asp in turn forms an amide bond with the carboxy group of the protracting moiety, or with the carboxy group of, e.g., an OEG molecule, if present, or with the beta-carboxy group of, e.g., another Asp, if present.

Chem. 9 may also be referred to as alpha-Asp, or briefly aAsp, or simply Asp, due to the fact that it is the alpha carboxy group of the amino acid aspartic acid which is here used for connection to another linker element, or to the epsilon-amino group of lysine.

The above structures of Chem. 8 and Chem. 9 cover the L-form, as well as the D-form of Asp. The L-form may be designated beta-L-Asp or bLAsp, whereas the D-form may be designated beta-D-Asp or bDAsp. In particular embodiments, Chem. 8 and/or Chem. 9 is/are, independently, a) in the L-form, or b) in the D-form.

In one embodiment, each linker of the derivative of the invention further comprise, independently or in combination with other linker elements, the following third linker element:

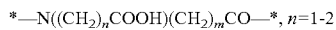  Chem. 10 in which n and m is an integer in the range of 1-2. This linker element may be designated IDA.

In one embodiment, each linker of the derivative of the invention, when the albumin binding moiety is attached by reductive alkylation further comprise, independently or in combination with other linker elements, the following linker element:

  Chem. 11

This linker element may be designated CPH.

In still further particular embodiments the linker has a) from 5 to 41 C-atoms; and/or b) from 4 to 28 hetero atoms.

Particular and non-limiting examples of hetero atoms are N-, and O-atoms. H-atoms are not hetero atoms.

Alternatively, the linker moiety, if present, has from 5 to 30 C-atoms, preferably from 5 to 25 C-atoms, more preferably from 5 to 20 C-atoms, or most preferably from 5 to 17 C-atoms. In additional preferred embodiments, the linker moiety, if present, has from 4 to 20 hetero atoms, preferably from 4 to 18 hetero atoms, more preferably from 4 to 14 hetero atoms, or most preferably from 4 to 12 hetero atoms.

Alternatively, the linker comprises at least one OEG molecule, and/or at least one glutamic acid residue, or rather the corresponding radicals.

In one embodiment, each linker consists of one time Chem. 6 and two times Chem. 5, interconnected via amide bonds and in the sequence indicated, the linker being connected at its free amino end to the free carbonyl group of the protracting moiety, and at its free carbonyl end to a B29 lyseine residue, a A22K lysine residue or the N-terminal of the A and/or B chain of an insulin.

In one embodiment one or more albumin binding moieties are attached to an insulin by acylation.

In one embodiment one or more albumin binding moieties are attached to an insulin by reductive alkylation.

One embodiment is a method for substituting an insulin or insulin derivative according to this invention with an albumin binding moiety by reductive alkylation.

In one embodiment an insulin is substituted according to this invention in two steps, in a first step one or more albumin binding moieties are attached to an insulin by acylation and in a second step one or more albumin binding moieties are attached by reductive alkylation to the insulin derivative achieved in the first step.

In one embodiment an insulin is substituted according to this invention in two steps, in a first step one or more albumin binding moieties are attached to an insulin by reductive alkylation and in a second step one or more albumin binding moieties are attached by acylation to the insulin derivative achieved in the first step.

In one embodiment an amine in the N-terminal of the A and/or B chain of the inulin reacts with an aldehyde function in the albumin binding moiety.

In one embodiment an insulin or insulin derivative according to this invention is substituted with an albumin binding moiety by reductive alkylation.

In one embodiment an insulin or insulin derivative according to this invention is substituted with one or more albumin binding moieties, by reductive alkylation using a reducing agent.

In one embodiment an insulin or insulin derivative according to this invention is substituted with one or more albumin binding moieties, by reductive alkylation using $NaCNBH_3$ as reducing agent.

One embodiment is a method for substituting an insulin or insulin derivative according to this invention with an albumin binding moiety by reductive alkylation, wherein $NaCNBH_3$ is used as reducing agent.

One embodiment is a method for substituting an insulin or insulin derivative according to this invention with an albumin binding moiety at said insulin's N-terminal amino acid residue in said insulin's A and/or B chain.

One embodiment of the present invention is a method for substituting an insulin or insulin derivative according to this invention with an albumin binding moiety at said insulin's N-terminal amino acid residue in said insulin's A and/or B chain, wherein $NaCNBH_3$ is used as reducing agent.

In one embodiment, the at least two side chains of the present invention are similar.

In one embodiment, the at least two albumin binding moieties of the present invention (i.e. the entire side chains) are similar.

In one embodiment, the protracting moieties of each albumin binding moiety are similar.

The term "similar" as used herein, referring to the at least two side chains or albumin binding moieties of the present invention, means that the combination of protracting moieties and linkers are the same (e.g. $Z=Z^1$, n=m and $X=X^1$, Chem. 1).

The term "similar" as used herein, referring to the protracting moieties of the at least two side chains of the present invention, means that the combination of protracting moieties are the same in the side chains of the insulin derivative (e.g. $X=X^1$).

The term "similar" as used herein, referring to the protracting moieties of the at least two albumin binding moieties of the present invention, means that the combination of protracting moieties are the same in the albumin binding moieties of the insulin derivative (e.g. $X=X^1$).

In one embodiment, the combination of linker elements of each side chain or albumin binding moiety are similar (e.g. for one insulin derivative according to this invention, if $e_1$-$e_2$=gDGlu-aLAsp combination for Z, $e_1$-$e_2$ for $Z_1$ is also a gDGlu-aLAsp combination).

In one embodiment, the combination of linker elements in each side chain or albumin binding moiety are not similar (e.g. for one insulin derivative according to this invention, if $e_1$-$e_2$ is a gDGlu-aLAsp combination for Z, $e_1$-$e_2$ for $Z_1$ is another combination of linker elements than a gDGlu-aLAsp combination, e.g. gDGlu-OEG).

In one embodiment, the combination of linker elements in the linkers (if present) of the at least two side chains of the present invention are not similar (e.g. for one insulin derivative according to this invention, if $e_1$-$e_2$ is a gDGlu-aLAsp combination for Z, $e_1$-$e_2$ for $Z_1$ is another combination of linker elements than a gDGlu-aLAsp combination, e.g. gDGlu-OEG) and the protracting moiety are not similar (e.g. X is not the same fatty diacid as $X_1$).

In one embodiment, the insulin derivative according to this invention is in the form of a pharmaceutically acceptable salt.

In one embodiment the salt may be a basic salt, an acid salt, or it may be neither nor (i.e. a neutral salt). Basic salts produce hydroxide ions and acid salts produce hydronium ions in water.

The salts of the insulin derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

In one embodiment, an insulin derivative according to the invention is used as a pharmaceutical.

In one embodiment, an insulin derivative according to the invention is used as a medicament.

In one embodiment, an insulin derivative according to the invention is used as a medicament for delaying or preventing disease progression in type 2 diabetes.

In one embodiment of the invention, the insulin derivative is for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders is provided.

In one embodiment, the invention is related to a method for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, coronary heart disease and other cardiovascular disorders, stroke, the method comprising administering to a patient in need of such treatment an effective amount for such treatment of an insulin derivative according to the invention.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

In one embodiment, an insulin derivative according to the invention is used for the preparation of a medicament for the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" according to the invention is herein to be understood as human insulin or an insulin from another species such as porcine or bovine insulin.

"A soluble insulin" according to the invention is herein to be understood as an insulin which is soluble in an aqueous solutions, including but not limited to water.

In one embodiment an insulin according to the present invention is soluble in water. In one embodiment an insulin according to the present invention is soluble aqueous solutions. In one embodiment an insulin according to the present invention is soluble in aqueous solutions with a pH ranging from pH 6 to 9. In one embodiment an insulin according to the present invention is soluble in aqueous solutions with a pH ranging from pH 7 to 8. In one embodiment an insulin according to the present invention is soluble in aqueous solutions with a pH ranging from pH 7.2 to 7.8. In one embodiment an insulin according to the present invention is soluble aqueous solutions with a pH ranging from pH 7.2 to 7.6. In one embodiment an insulin according to the present invention is soluble in aqueous solutions with a pH ranging from pH 7.4 to 7.6. In one embodiment an insulin according to the present invention is soluble in aqueous solutions with a pH ranging from pH 7.4 to 7.8. In one embodiment an insulin according to the present invention is soluble in pH basic aqueous solutions. In one embodiment an insulin according to the present invention is soluble in pH neutral aqueous solutions. In one embodiment an insulin according to the present invention is soluble in aqueous solutions being neutral or 1-2 pH units below neutral. In one embodiment an insulin according to the present invention is soluble in aqueous solutions being neutral or 1 pH units below neutral.

In one embodiment an insulin according to this invention has a solubility of between 0.5 mM and 8 mM. In one embodiment an insulin according to this invention has a solubility of between 0.6 mM and 7.2 mM. In one embodiment an insulin according to this invention has a solubility of at least 0.6 mM. In one embodiment an insulin according to this invention has a solubility of at least 0.8 mM. In one embodiment an insulin according to this invention has a solubility of at least 1.0 mM. In one embodiment an insulin according to this invention has a solubility of at least 1.2 mM. In one embodiment an insulin according to this invention has a solubility of at least 1.4 mM. In one embodiment an insulin according to this invention has a solubility of at least 1.8 mM. In one embodiment an insulin according to this invention has a solubility of at least 2.0 mM. In one embodiment an insulin according to this invention has a solubility of at least 2.2 mM. In one embodiment an insulin according to this invention has a solubility of at least 2.4 mM. In one embodiment an insulin according to this invention has a solubility of at least 2.6 mM. In one embodiment an insulin according to this invention has a solubility of at least 2.8 mM. In one embodiment an insulin according to this invention has a solubility of at least 3.0 mM. In one embodiment an insulin according to this invention has a solubility of at least 3.2 mM. In one embodiment an insulin according to this invention has a solubility of at least 3.4 mM. In one embodiment an insulin according to this invention has a solubility of at least 3.6 mM. In one embodiment an insulin according to this invention has a solubility of at least 3.8 mM. In one embodiment an insulin according to this invention has a solubility of at least 4.0 mM. In one embodiment an insulin according to this invention has a solubility of at least 4.2 mM. In one embodiment an insulin according to this invention has a solubility of at least 4.4 mM. In one embodiment an insulin according to this invention has a solubility of at least 4.6 mM. In one embodiment an insulin according to this invention has a solubility of at least 4.8 mM. In one embodiment an insulin according to this invention has a solubility of at least 5.0 mM. In one embodiment an insulin according to this invention has a solubility of at least 5.2 mM. In one embodiment an insulin according to this invention has a solubility of at least 5.4 mM. In one embodiment an insulin according to this invention has a solubility of at least 5.6 mM. In one embodiment an insulin according to this invention has a solubility of at least 5.8 mM. In one embodiment an insulin according to this invention has a solubility of at least 6.0 mM. In one embodiment an insulin according to this invention has a solubility of at least 6.2 mM. In one embodiment an insulin according to this invention has a solubility of at least 6.4 mM. In one embodiment an insulin according to this invention has a solubility of at least 6.6 mM. In one embodiment an insulin according to this invention has a solubility of at least 6.8 mM. In one embodiment an insulin according to this invention has a solubility of at least 7.0 mM. In one embodiment an insulin according to this invention has a solubility of at least 7.2 mM. In one embodiment an insulin according to this invention has a solubility of at least 7.4 mM. In one embodiment an insulin according to this invention has a solubility of at least 7.6 mM. In one embodiment an insulin according to this invention has a solubility of at least 7.8 mM. In one embodiment an insulin according to this invention has a solubility of at least 8.0 mM.

The term "insulin peptide" as used herein means a peptide which is either human insulin or an analogue or a derivative thereof with insulin activity.

The term "insulin derivative" as used herein means a chemically modified insulin, wherein the modification(s) are in the form of attachment of amides, carbohydrates, alkyl groups, acyl groups, esters, PEGylations, and the like. Examples of derivatives of human insulin according to the invention are A22N$^\alpha$-hexadecandioyl-γ-L-glutamyl B29N$^\epsilon$-hexadecandioyl-γ-L-glutamyl A22K desB30 human insulin, A22N$^\epsilon$-octadecandioyl-γ-L-glutamyl-OEG-OEG B29N$^\epsilon$-octadecandioyl-γ-L-glutamyl-OEG-OEG A22K desB30 human insulin, A22N$^\epsilon$-tetradecandioyl-γ-L-glutamyl B29N$^\epsilon$-tetradecandioyl-γ-L-glutamyl A22K desB30 human insulin, A22N$^\epsilon$-octadecandioyl-γ-D-glutamyl B29N$^\epsilon$-octadecandioyl-γ-D-glutamyl A22K desB30 human insulin, A22N$^\epsilon$-hexadecandioyl-γ-L-glutamyl B29N$^\epsilon$-hexadecandioyl-γ-L-glutamyl A14E A22K B25H desB30 human insulin, A22N$^\epsilon$-octadecandioyl-γ-L-glutamyl-OEG-OEG B29N$^\epsilon$-octadecandioyl-γ-L-glutamyl-OEG-OEG A14E A22K B25H desB30 human insulin, A1N$^\alpha$-hexadecandioyl-γ-L-glutamyl B29N$^\epsilon$-hexadecandioyl-γ-L-glutamyl A14E B25H desB30 human insulin, A1N$^\alpha$-hexadecandioyl-γ-L-glutamyl B29N$^\epsilon$-hexadecandioyl-γ-L-glutamyl desB30 human insulin, A1N$^\alpha$-octadecandioyl-γ-L-glutamyl-OEG-OEG B29N$^\epsilon$-octadecandioyl-γ-L-glutamyl-OEG-OEG A14E B25H desB30 human insulin, A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB27 desB30 human insulin, A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB30 human insulin, A1N$^\alpha$-hexadecandioyl-γ-L-glutamyl-OEG-OEG-4-aminomethyl-benzyl B1N$^\alpha$-hexadecandioyl-γ-L-glutamyl-OEG-OEG-4-aminomethyl-benzyl A14E B25H desB27 desB30 human insulin, A1N$^\alpha$-tetradecandioyl-γ-L-glutamyl-OEG-OEG-4-aminomethyl-benzyl B1N$^\alpha$-tetradecandioyl-γ-L-glutamyl-OEG-OEG-4-aminomethyl-benzyl A14E B25H desB27 desB30 human insulin, A1N$^\alpha$-hexadecandioyl-γ-L-glutamyl-OEG-OEG-4-aminomethyl-benzyl B1N$^a$-hexadecandioyl-γ-L-glutamyl-OEG-OEG-4-aminomethyl-benzyl A14E B25H desB30 human insulin, B1N$^\alpha$-octadecandioyl-γ-L-glutamyl-OEG-OEG-aminomethyl-benzyl B29N$^\epsilon$-octadecandioyl-γ-L-glutamyl-OEG-OEG A14E B25H desB30 human insulin, A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl B29N$^\epsilon$octadecandioyl-γ-L-glutamyl-OEG-OEG A14E B25H desB30 human insulin, A1N$^\alpha$-octadecandioyl-N-carboxymethyl-beta-alanyl B29N$^\epsilon$-octadecandioyl-N-carboxymethyl-beta-alanyl A14E B25H desB30 human insulin, A1N$^\alpha$octadecandioyl-N-2-carboxyethyl-glycyl B29N$^\epsilon$-octadecandioyl-N-2-carboxyethyl-glycyl A14E B25H desB30 human insulin, A1N$^\alpha$-octadecandioyl-N-carboxymethyl-beta-alanyl A22N$^\epsilon$—N-octadecandioyl-N-carboxymethyl-beta-alanyl A22K B29R desB30 human insulin, A22N$^\epsilon$-hexadecandioyl-γ-L-glutamyl-OEG-OEG B29N$^\epsilon$-hexadecandioyl-γ-L-glutamyl-OEG-OEG A14E B25H desB30 human insulin, A1N$^\alpha$-hexadecandioyl-γ-L-glutamyl-OEG-OEG B29N$^\epsilon$-hexadecandioyl-γ-L-glutamyl-OEG-OEG A14E B25H desB30 human insulin, A1N$^\alpha$-hexadecandioyl-γ-L-glutamyl-OEG-OEG B29N$^\epsilon$-hexadecandioyl-γ-L-glutamyl-OEG-OEG A14E B16H B25H desB30 human insulin, A1N$^\alpha$-octadecandioyl-γ-L-glutamyl-OEG-OEG B1N$^\alpha$-octadecandioyl-γ-L-glutamyl-OEG-OEG A14E B25H B29R desB30 human, A22N$^\epsilon$-eicosandioyl-γ-L-glutamyl-OEG-OEG B29N$^\epsilon$-eicosandioyl-γ-L-glutamyl-OEG-OEG A14E A22K B25H desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG A14E B16H B25H desB30 human insulin, B1N$^\alpha$-(octadecandioyl-γ-L-glutamyl-OEG-OEG-4-aminomethyl-benzyl B29N$^\epsilon$-octadecandioyl-γ-L-glutamyl-OEG-OEG A14E B25H desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG A14E B25H desB27 desB30 human insulin, A22N$^\epsilon$-4-carboxyphenoxy-decanoyl-γ-L-glutamyl-OEG-OEG B29N$^\epsilon$-4-carboxyphenoxy-decanoyl-γ-L-glutamyl-OEG-OEG A14E A22K B25H desB30 human insulin, A1N$^\alpha$-octadecandioyl-gamma-L-glutamyl-OEG-OEG B29N$^\epsilon$-octadecandioyl-gamma-L-glutamyl-OEG-OEG A14E B16H B25H desB30 human insulin, A1N$^\alpha$-octadecandioyl-gamma-L-glutamyl-OEG-OEG B29N$^\epsilon$-octadecandioyl-gamma-L-glutamyl-OEG-OEG A14E B16H desB27 desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin, A1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG A14E desB27 desB30 human insulin, B1N$^\alpha$-octadecandioyl-γ-L-glutamyl-OEG-OEG-OEG-OEG-4-aminomethyl-benzyl B29N$^\epsilon$-octadecandioyl-γ-L-glutamyl-OEG-OEG-OEG-OEG A14E desB27 desB30 human insulin.

The term "insulin analogue" as used herein means a modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modification relative to human insulin.

Modifications in the insulin molecule are denoted stating the chain (A or B), the position, and the one or three letter code for the amino acid residue substituting the native amino acid residue.

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. The connecting peptide includes two terminal dibasic amino acid sequence, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., A14E A22K desB30 human insulin is an analogue of human insulin where the amino acid in position 14 in the A chain is substituted with glutamic acid, the amino acid in position 22 in the A chain is substituted with lysine, and the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

Herein, the term "amino acid residue" is an amino acid from which, formally, a hydroxy group has been removed from a carboxy group and/or from which, formally, a hydrogen atom has been removed from an amino group.

Amino acids exist in the stereoisomeric form of either D (dextro) or L (levo). The D and L refer to the absolute confirmation of optically active compounds. With the exception of glycine, all other amino acids are mirror images that can not be superimposed. Most of the amino acids found in nature are of the L-type. Hence, eukaryotic proteins are always composed of L-amino acids although D-amino acids are found in bacterial cell walls and in some peptide antibiotics. At least 300 amino acids have been described in nature but only twenty of these are typically found as components in human peptides and proteins. Twenty standards amino acids are used by cells in peptide biosynthesis, and these are specified by the general genetic code. The twenty standard amino acids are Alanine (Ala), Valine (Val), Leucine (Leu), Isoleucine (Ile), Phenylalanine (Phe), Tryptophan (Trp), Methionine (Met), Proline (Pro), Apartic acid (Asp), Gltamic acid (Glu), Glycine (Gly), Serine (Ser), Threonine (Thr), Cysteine (Cys), Tyrosine (Tyr), Apsagine (Asn), Glutamine (Gln), Lysine (Lys), Arginine (Arg) and Histidine (His).

Examples of insulin analogues are such wherein Tyr (Y) in position 14 of the A chain is substituted with Glu (E) and/or Lys (K) at position B29 is substituted with Pro (P), Arg (R). Furthermore, Asn (N) at position B3 may be substituted with Lys (K). Also one or more amino acids may be added to the C-terminal of the A-chain and/or B-chain such as, e.g., Lys (K). The amino acid in position B1 may be substituted with Glu (E). The amino acid in position B16 may be substituted with His (H). Further examples of insulin analogues are the deletion analogues, e.g., analogues where the B30 amino acid in human insulin has been deleted (desB30 human insulin), desB28-B30 human insulin and desB27 human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position B25 is His(H) and which optionally further comprises one or more additional mutations are further examples of insulin analogues. Insulin analogues of human insulin wherein the amino acid residue in position A22 is Lys (K) and/or wherein the insulin analogue is further extended in the C-terminal with two Arg (R) residues are also examples of insulin analogues.

Further examples of insulin analogues include: desB30 human insulin, A22K desB30 human insulin, A14E A22K desB30 human insulin, A14E A22K B25H B29R desB30 human insulin, A14E A22K B25H desB30 human insulin A14E B25H desB27 desB30 human insulin, A14E B25H desB30 human insulin, A14E B16H desB30 human insulin, A14E B16H B25H desB30 human insulin B28D human insulin, A22K B29R desB30 human insulin, B3K B28E human insulin, B28D desB30 human insulin, A22K B29P desB30 human insulin, B28K B29P human insulin, B28K B29P desB30 human insulin, B3K B28E desB30 human insulin, A14E desB27 desB30 human insulin and A14E B16H desB27 desB30 human insulin Insulin Receptor Binding Assay (HIRspa):

The affinity of the insuloin derivatives of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 mL of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 mL of SPA-beads and binding buffer to a total of 12 mL. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the Graph-Pad Prism 2.01 (Graph Pad Software, San Diego, Calif.) and affinities are expressed relative (in percentage (%)) to the affinity of human insulin.

A related assay is also used wherein the binding buffer also contains 1.5% HSA in order to mimic physiological conditions Pharmacokinetics Assay, Intravenous Rat PK:

Anaesthetized rats are dosed intravenously (i.v.) with insulin derivatives at various doses and plasma concentrations of the employed compounds are measured using immunoassays or mass spectrometry at specified intervals for 4 hours or more post-dose. Pharmacokinetic parameters are subsequently calculated using WinNonLin Professional (Pharsight Inc., Mountain View, Calif., USA).

Non-fasted male Wistar rats (Taconic) weighing approximately 200 gram are used.

Body weight is measured and rats are subsequently anaesthetized with Hypnorm/Dormicum (each compound is separately diluted 1:1 in sterile water and then mixed; prepared freshly on the experimental day). Anesthesia is initiated by 2 mL/kg Hypnorm/Doricum mixture sc followed by two maintenance doses of 1 mL/kg sc at 30 min intervals and two maintenance doses of 1 mL/kg sc with 45 min intervals. If required in order to keep the rats lightly anaesthetized throughout a further dose(s) 1-2 mL/kg sc is supplied. Weighing and initial anaesthesia is performed in the rat holding room in order to avoid stressing the animals by moving them from one room to another.

Albumin Binding Assay, Retention Time (RT)

Measurements of drug-protein binding by using immobilized human serum albumin chromatography-mass spectrometry.

Albumin binding, measured by LC-MS as retention time (Rt) on immobilized HSA-column.

The solvent was used in the following order:

A: 50 mM Ammonium Acetate pH 7.4 (3,854 g/1 L) freshly prepared

B: 100% 2-propanol

| Time (min) | A solvent (%) | B solvent (%) | flow (mL/min) |
|---|---|---|---|
| 0 | 100 | 0 | 0.7 |
| 5 | 65 | 35 | 0.7 |
| 15 | 60 | 40 | 0.7 |
| 16 | 100 | 0 | 0.7 |
| 20 | 100 | 0 | 0.7 |

The HPLC 1100 system (CTC PAL autosampler) was aligned as follows:

HPLC-Column: Chiral HSA 50×3.0 mm 5 μm (Chromtech cat no: HSA 50.3 06-F)

UV detector: 280 nm

Column Temperature: 45° C.

Compound injection: 10 μL, 10 μM

Split 1:4 (MS:LC)

The LC/MSD Trap XCT was aligned as follows:

Ion Source Type: ESI

Polarity: Positive

Dry Temp: 325° C.

Nebulizer: 40.00 psi

Dry Gas: 8.00 L/min

Production of Insulin

The production of polypeptides, e.g., insulins, is well known in the art. The insulin or insulin analogue used as part of the insulin derivative may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999. The insulin or insulin analogue may also be produced by a method which comprises culturing a host cell containing a DNA sequence encoding the analogue and capable of expressing the insulin or insulin analogue in a suitable nutrient medium under conditions permitting the expression of the insulin or insulin analogue. Several recombinant methods may be used in the production of human insulin and human insulin analogues. Examples of methods which may be used in the production of insulin in microorganisms such as, e.g., *Escherichia coli* and *Saccharomyces cerevisiae* are, e.g., disclosed in WO2008/034881.

Typically, the insulin or insulin analogue is produced by expressing a DNA sequence encoding the insulin or insulin analogue in question or a precursor thereof in a suitable host cell by well-known technique as disclosed in e.g. EP1246845 or WO2008/034881.

The insulin or insulin analogue may be expressed with an N-terminal extension as disclosed in EP 1,246,845. After secretion to the culture medium and recovery, the insulin precursor will be subjected to various in vitro procedures to remove the possible N-terminal extension sequence and connecting peptide to give the insulin or insulin analogue. Such methods include enzymatic conversion by means of trypsin or an *Achromobacter lyticus* protease in the presence of an L-threonine ester followed by conversion of the threonine ester of the insulin or insulin analogue into insulin or insulin analogue by basic or acid hydrolysis as described in U.S. Pat. No. 4,343,898 or U.S. Pat. No. 4,916,212

Examples of N-terminal extensions of the type suitable in the present invention are disclosed in U.S. Pat. No. 5,395,922 and EP0765395.

For insulin analogues comprising non-natural amino acid residues, the recombinant cell should be modified such that the non-natural amino acids are incorporated into the analogue, for instance by use of tRNA mutants. Hence, briefly, the insulin or insulin analogue according to the invention are prepared analogously to the preparation of known insulin analogues.

Protein Purification

The insulin or insulin analogue used as part of the insulin derivative of the invention are recovered from the cell culture medium. The insulin or insulin analogue of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-insulin or anti-insulin analogue antibody column. Additional purification may be achieved by conventional chemical purification means, such as high performance liquid chromatography. Other methods of purification, including barium citrate precipitation, are known in the art, and may be applied to the purification of the novel insulin or insulin analogue described herein (see, for example, Scopes, R., Protein Purification, Springer-Verlag, N.Y., 1982).

Pharmaceutical Formulations

Pharmaceutical compositions containing an insulin derivative according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

For parenteral administration, an insulin derivative of this invention is formulated analogously with the formulation of known insulins. Furthermore, for parenterally administration, an insulin derivative of this invention is administered analogously with the administration of known insulins and the physicians are familiar with this procedure.

Parenteral administration can be performed by means of a syringe, optionally a pen-like syringe. Alternatively, parenteral administration can be performed by means of an infusion pump.

Injectable compositions containing an insulin derivative of this invention can be prepared using the conventional techniques of the pharmaceutical industry which involve dissolving and mixing the ingredients as appropriate to give the desired end product. Thus, according to one procedure, an insulin derivative of this invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. The tablets may be uncoated or they may be coated by known techniques to delay disintegration or release of the therapeutically active polypeptide.

The orally administrable formulations of the present invention may be prepared and administered according to methods well known in pharmaceutical chemistry, see Remington's Pharmaceutical Sciences, 17$^{th}$ ed. (A. Osol ed., 1985).

The insulin derivative preparations of this invention are used similarly to the use of the known insulin preparations. The Following is a Non-Limiting List of Aspect Further Comprised within the Scope of the Invention:

1) An insulin derivative or a pharmaceutically acceptable salt thereof comprising at least 2 albumin binding moieties, wherein each albumin binding moiety comprises a fatty diacid substitution and wherein one carboxy group from each of said fatty diacid substitutions is attached, optionally via a linker, to an insulin.
2) An insulin derivative or a pharmaceutically acceptable salt thereof comprising at least 3 albumin binding moieties, wherein each albumin binding moiety comprises a fatty diacid substitution and wherein one carboxy group from each of said fatty diacid substitutions is attached, optionally via a linker, to an insulin.
3) An insulin derivative or a pharmaceutically acceptable salt thereof comprising 2 or 3 albumin binding moieties, wherein each albumin binding moiety comprises a fatty diacid substitution and wherein one carboxy group from each of said substitutions is attached, optionally via a linker, to an insulin.
4) An insulin derivative or a pharmaceutically acceptable salt thereof comprising 2 albumin binding moieties, wherein each albumin binding moiety comprises a fatty diacid substitution and wherein one carboxy group from each of said fatty diacid substitutions is attached, optionally via a linker, to an insulin.
5) An insulin derivative or a pharmaceutically acceptable salt comprising 3 albumin binding moieties, wherein each albumin binding moiety comprises a fatty diacid substitution and wherein one carboxy group from each of said fatty diacid substitutions is attached, optionally via a linker, to an insulin.
6) An insulin derivative or a pharmaceutically acceptable salt thereof, according to any one of the previous aspects, comprising at least 3 albumin binding moieties, wherein each albumin binding moiety comprises a fatty diacid substitution and wherein one carboxy group from each of said fatty diacid substitutions is attached, optionally via a linker, to an insulin.
7) An insulin derivative or a pharmaceutically acceptable salt thereof, according to any one of the previous aspects comprising 2 or 3 albumin binding moieties, wherein each albumin binding moiety comprises a fatty diacid substitution and wherein one carboxy group from each of said substitutions is attached, optionally via a linker, to an insulin.
8) An insulin derivative or a pharmaceutically acceptable salt thereof, according to any one of the previous aspects, comprising 2 albumin binding moieties, wherein each albumin binding moiety comprises a fatty diacid substitution and wherein one carboxy group from each of said fatty diacid substitutions is attached, optionally via a linker, to an insulin.
9) An insulin derivative or a pharmaceutically acceptable salt thereof, according to any one of the previous aspects, comprising 3 albumin binding moieties, wherein each albumin binding moiety comprises a fatty diacid substitution and wherein one carboxy group from each of said fatty diacid substitutions is attached, optionally via a linker, to an insulin.
10) An insulin derivative or a pharmaceutically acceptable salt thereof of the general formula

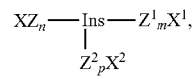

wherein
a. Ins represents an insulin comprising a B29 lysine or B29 arginine residue and/or a A22 lysine residue
b. X, X$^1$ and X$^2$ is a fatty diacid substitution and X$^2$ is optional
c. Z, Z$^1$ and Z$^2$ is a linker between Ins and X, X$^1$ and X$^2$, respectively and
d. n, m and p is zero or 1.
11) An insulin derivative or a pharmaceutically acceptable salt thereof according to any of the preceding aspects of the general formula

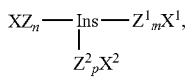

wherein
  a. Ins represents an insulin comprising a B29 lysine or B29 arginine residue and/or a A22 lysine residue
  b. X, $X^1$ and $X^2$ is a fatty diacid substitution and $X^2$ is optional
  c. Z, $Z^1$ and $Z^2$ is a linker between Ins and X, $X^1$ and $X^2$, respectively and
  d. n, m and p is zero or 1.

12) An insulin derivative or a pharmaceutically acceptable salt thereof according to any of the preceding aspects of the general formula

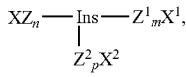

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: B29 lysine, A22 lysine, N-terminal of the A chain, N-terminal of the B-chain.
  c. Z, $Z^1$ and $Z^2$ is a linker between Ins and X, $X^1$ and $X^2$, respectively and
  d. n, m and p is zero or 1.

13) An insulin derivative or a pharmaceutically acceptable salt thereof according to any of the preceding aspects of the general formula

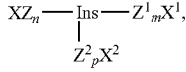

wherein
  a. Ins represents an insulin comprising a B29 arginine residue and a A22 lysine residue,
  b. X, $X^1$ and $X^2$ is a fatty diacid substitution, and X is located at said A22 lysine residue and $X^1$ is located the N-terminal of the A chain and $X^2$ is not present,
  c. Z, $Z^1$ and $Z^2$ is a linker between Ins and X, $X^1$ and $X^2$, respectively and
  d. n and m is 1 or zero and p is zero.

14) An insulin derivative or a pharmaceutically acceptable salt thereof according to any of the preceding aspects of the general formula

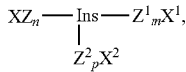

wherein
  a. Ins represents an insulin comprising a B29 arginine residue and a A22 lysine residue,
  b. X, $X^1$ and $X^2$ is a fatty diacid substitution, and X is located at said A22 lysine residue and $X^1$ is located the N-terminal of the B chain, and $X^2$ is not present,
  c. Z, $Z^1$ and $Z^2$ is a linker between Ins and X, $X^1$ and $X^2$, respectively and
  d. n and m is 1 or zero and p is zero.

15) An insulin derivative or a pharmaceutically acceptable salt thereof according to any of the preceding aspects of the general formula

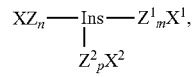

wherein
  a. Ins represents an insulin comprising a B29 lysine,
  b. X, $X^1$ and $X^2$ is a fatty diacid substitution, and X is located at said B29 lysine residue and $X^1$ is located at said N-terminal of the A chain, and $X^2$ is not present
  c. Z, $Z^1$ and $Z^2$ is a linker between Ins and X, $X^1$ and $X^2$, respectively and
  d. n and m is 1 or zero and p is zero.

16) An insulin derivative or a pharmaceutically acceptable salt thereof according to any of the preceding aspects of the general formula

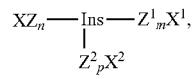

wherein
  a. Ins represents an insulin comprising a B29 lysine residue and/or a A22 lysine residue,
  b. X, $X^1$ and $X^2$ is a fatty diacid substitution, and X is located at said B29 lysine residue and $X^1$ is located the N-terminal of the B chain, and $X^2$ is not present
  c. Z, $Z^1$ and $Z^2$ is a linker between Ins and X, $X^1$ and $X^2$, respectively and
  d. n and m is 1 or zero and p is zero.

17) An insulin derivative or a pharmaceutically acceptable salt thereof according to any of the preceding aspects of the general formula

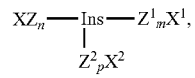

wherein
  a. Ins represents an insulin comprising a B29 lysine residue and a A22 lysine residue,
  b. X, $X^1$ and $X^2$ is a fatty diacid substitution, and X is located at said B29 lysine residue and $X^1$ is located at said A22 lysine residue, and $X^2$ is not present
  c. Z, $Z^1$ and $Z^2$ is a linker between Ins and X, $X^1$ and $X^2$, respectively and
  d. n and m is 1 or zero and p is zero.

18) An insulin derivative or a pharmaceutically acceptable salt thereof according to any of the preceding aspects of the general formula

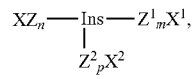

wherein
   a. Ins represents an insulin comprising a B29 arginine residue and/or a A22 lysine residue,
   b. X, X¹ and X² is a fatty diacid substitution, and X is located at said N-terminal in the A chain and X¹ is located at said N-terminal in the B chain, and X² is not present
   c. Z, Z¹ and Z² is a linker between Ins and X, X¹ and X², respectively and
   d. n and m is 1 or zero and p is zero.

19) An insulin derivative or a pharmaceutically acceptable salt thereof according to any of the preceding aspects of the general formula

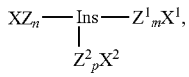

wherein
   a. Ins represents an insulin comprising a B29 lysine,
   b. X, X¹ and X² is a fatty diacid substitution, and X is located at said B29 lysine residue and X¹ is at said N-terminal of the A chain, and X² is located at said N-terminal in the B chain
   c. Z, Z¹ and Z² is a linker between Ins and X, X¹ and X², respectively and
   d. n, m and p is zero or 1.

20) An insulin derivative or a pharmaceutically acceptable salt thereof according to any of the preceding aspects of the general formula

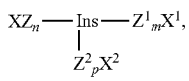

wherein
   a. Ins represents an insulin comprising a B29 arginine residue and a A22 lysine residue,
   b. X, X¹ and X² is a fatty diacid substitution, and X is located at said A22 lysine residue and X¹ is at said N-terminal of the A chain, and X² is located at said N-terminal of the B chain
   c. Z, Z¹ and Z² is a linker between Ins and X, X¹ and X², respectively and
   d. n, m and p is zero or 1.

21) An insulin derivative or a pharmaceutically acceptable salt thereof of the general formula $XZ_n\text{-Ins-}Z^1{}_mX^1$, wherein
   a. Ins represents an insulin comprising a B29 lysine or B29 arginine residue and/or a A22 lysine residue,
   b. X and X¹ is a fatty diacid substitution,
   c. Z and Z¹ is a linker between Ins and X and X¹ respectively, and
   d. n and m is zero or 1.

22) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 lysine or B29 arginine residue and/or a A22 lysine residue,
   b. X and X¹ is a fatty diacid substitution,
   c. Z and Z¹ is a linker between Ins and X and X¹ respectively, and
   d. n and m is zero or 1.

23) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 lysine or B29 arginine residue and/or a A22 lysine residue,
   b. X and X¹ is a fatty diacid substitution and respectively located in a position selected from the group consisting of: B29 lysine, A22 lysine, N-terminal of the A chain, N-terminal of the B-chain
   c. Z and Z¹ is a linker between Ins and X and X¹ respectively, and
   d. n and m is zero or 1.

24) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 arginine residue and a A22 lysine residue,
   b. X and X¹ is a fatty diacid substitution fatty diacid substitution, and X is located at said A22 lysine residue and X¹ is located the N-terminal of the A chain,
   c. Z and Z¹ is a linker between Ins and X and X¹ respectively, and
   d. n and m is zero or 1.

25) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 arginine residue and a A22 lysine residue,
   b. X and X¹ is a fatty diacid substitution, and X is located at said A22 lysine residue and X¹ is located the N-terminal of the B chain,
   c. Z and Z¹ is a linker between Ins and X and X¹ respectively, and
   d. n and m is zero or 1.

26) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 lysine residue,
   b. X and X¹ is a fatty diacid substitution, and X is located at said B29 lysine residue and X¹ is located at said N-terminal of the A chain,
   c. Z and Z¹ is a linker between Ins and X and X¹ respectively, and
   d. n and m is zero or 1.

27) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 lysine residue,
   b. X and X¹ is a fatty diacid substitution, and X is located at said B29 lysine residue and X¹ is located the N-terminal of the B chain,
   c. Z and Z¹ is a linker between Ins and X and X¹ respectively, and
   d. n and m is zero or 1.

28) An insulin derivative or a pharmaceutically acceptable salt thereof according to any of the preceding aspects of the general formula $XZ_n\text{-Ins-}Z^1{}_mX^1$, wherein
   a. Ins represents an insulin comprising a B29 lysine and a A22 lysine residue,
   b. X and X¹ is a fatty diacid substitution, and X is located at said B29 lysine residue and X¹ is located at said A22 lysine residue,
   c. Z and Z¹ is a linker between Ins and X and X¹ respectively, and
   d. n and m is zero or 1.

29) An insulin derivative or a pharmaceutically acceptable salt thereof according to any of the preceding aspects of the general formula $XZ_n$-Ins-$Z^1_m X^1$, wherein
   a. Ins represents an insulin comprising a B29 arginine residue,
   b. X and $X^1$ is a fatty diacid substitution, and X is located at said N-terminal of the A chain and $X^1$ is located at said N-terminal in the B chain,
   c. Z and $Z^1$ is a linker between Ins and X and $X^1$ respectively, and
   d. n and m is zero or 1.
30) An insulin derivative or a pharmaceutically acceptable salt thereof according to any of the preceding aspects, wherein said fatty diacid substitutions comprise 10 to 20 carbon atoms.
31) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is an integer from 10 to 20 and y is an integer from 6 to 14.

32) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is an integer from 14 to 20 and y is an integer from 6 to 10.

33) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is an integer from 14 to 18 and y is an integer from 8 to 10.

34) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is an integer from 14 to 16 and y is an integer from 10 to 12.

35) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is an integer from 14 to 20 and y is an integer from 6 to 12.

36) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is 12, 14, 16, 18 or 20 and y is 6, 8, 10, 12 or 14.

37) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is 14, 16, 18 or 20 and y is 8, 10 or 12.

38) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is 14, 16, 18 or 20 and y is 6, 8 or 10.

39) An insulin derivative or a pharmaceutically acceptable salt thereof according to any of the preceding aspects, wherein said fatty acid substitutions are selected from a group of protracting moieties selected from Chem. 1 and Chem. 2:

HOOC—(CH$_2$)$_x$—CO—*  Chem 1

HOOC—C$_6$H$_4$—O—(CH$_2$)$_y$—CO—*  Chem 2

Wherein x is 14, 16 or 18 and y is 8, 10 or 12.

40) An insulin derivative or a pharmaceutically acceptable salt thereof according to any of the preceding aspects, wherein said fatty diacid substitution is attached at an amino acid residue in said insulin, in a position selected from the group consisting of A1, A22, B1 and B29.

41) An insulin derivative according to any of the preceding aspects, wherein said fatty diacid substitution is attached to a lysine side-chain epsilon-amino group, or the N-terminal of the A and/or B chain of the insulin, respectively.

42) An insulin derivative or a pharmaceutically acceptable salt thereof according to any of the preceding aspects, wherein said fatty diacid substitutions are attached to amino acid residues of the insulin via a linker.

43) An insulin derivative or a pharmaceutically acceptable salt thereof according to any of the preceding aspects, wherein said linker (Z) comprises one or more linker elements (e).

44) An insulin derivative or a pharmaceutically acceptable salt thereof according to any of the preceding aspects, wherein said linker comprises one or more linker elements selected from the group consisting of: alpha-L-Glu, alpha-D-Glu, gamma-L-Glu, gamma-D-Glu, alpha-L-Asp, alpha-D-Asp, beta-L-Asp, beta-D-Asp, CPH, IDA and OEG.

45) An insulin derivative or a pharmaceutically acceptable salt thereof according to any of the preceding aspects, wherein said linker comprises two linker elements represented by the formula: $e_1$-$e_2$, wherein
  a. $e_1$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG
  b. $e_2$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG.

46) An insulin derivative or a pharmaceutically acceptable salt thereof according to any of the preceding aspects, wherein said linker comprises three linker elements represented by the formula: $e_1$-$e_2$-$e_3$, wherein
  a. $e_1$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG
  b. $e_2$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG
  c. $e_3$ is a linker element selected from the group consisting of alpha-L-Glu, alpha-D-Glu, gamma-L-Glu, gamma-D-Glu, alpha-L-Asp, alpha-D-Asp, beta-L-Aps, beta-D-Asp, CPH, IDA and OEG.

47) An insulin derivative or a pharmaceutically acceptable salt thereof according to any of the preceding aspects, wherein said linker comprises four linker elements represented by the formula: $e_1$-$e_2$-$e_3$-$e_4$, wherein
  a. $e_1$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG
  b. $e_2$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG
  c. $e_3$ is a linker element selected from the group consisting of alpha-L-Glu, alpha-D-Glu, gamma-L-Glu, gamma-D-Glu, alpha-L-Asp, alpha-D-Asp, beta-L-Aps, beta-D-Asp, CPH, IDA and OEG
  d. $e_4$ is a linker element selected from the group consisting of alpha-L-Glu, alpha-D-Glu, gamma-L-Glu, gamma-D-Glu, alpha-L-Asp, alpha-D-Asp, beta-L-Asp, beta-D-Asp, CPH, IDA and OEG.

48) An insulin derivative or a pharmaceutically acceptable salt thereof according to any of the preceding aspects, wherein said albumin binding moiety is located at the N-terminal of said insulin A and/or B-chain and wherein the linker comprises one or more CPH linker elements.

49) An insulin derivative according to any of the preceding aspects, wherein the albumin binding moieties of said insulin derivative are similar.

50) An insulin derivative or a pharmaceutically acceptable salt thereof according to any of the preceding aspects, wherein the insulin derivative is selected from the group consisting of a derivative of human insulin, a derivative of desB30 human insulin and a derivative of an insulin analogue.

51) An insulin derivative or a pharmaceutically acceptable salt thereof according to any of the preceding aspects, wherein the insulin is selected from the group consisting of desB30 human insulin, A22K desB30 human insulin, A14E A22K desB30 human insulin, A14E A22K B25H B29R desB30 human insulin, A14E A22K B25H desB30 human insulin A14E B25H desB27 desB30 human insulin, A14E B25H desB30 human insulin, A14E B16H desB30 human insulin, A14E B16H B25H desB30 human insulin B28D human insulin, A22K B29R desB30 human insulin, B3K B28E human insulin, B28D desB30 human insulin, A22K B29P desB30 human insulin, B28K B29P human insulin, B28K B29P desB30 human insulin and B3K B28E desB30 human insulin, A1N$^\alpha$-octadecandioyl-gamma-L-glutamyl-OEG-OEG B29N$^\epsilon$-octadecandioyl-gamma-L-glutamyl-OEG-OEG A14E B16H B25H desB30 human insulin, A1N$^\alpha$-octadecandioyl-gamma-L-glutamyl-OEG-OEG B29N$^\epsilon$-octadecandioyl-gamma-L-glutamyl-OEG-OEG A14E B16H desB27 desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin, A1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin, B1N$^\alpha$-octadecandioyl-γ-L-glutamyl-OEG-OEG-4-aminomethyl-benzyl, B29N$^\epsilon$-octadecandioyl-γ-L-glutamyl-OEG-OEG A14E desB27 desB30 human insulin, B1N$^\alpha$-octadecandioyl-γ-L-glutamyl-OEG-OEG-OEG-4-aminomethyl-benzyl B29N$^\epsilon$-octadecandioyl-γ-L-glutamyl-OEG-OEG-OEG-OEG A14E desB27 desB30 human insulin.

52) An insulin derivative or a pharmaceutically acceptable salt thereof according to any of the preceding aspects for the use as a medicament in the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

53) An insulin derivative or a pharmaceutically acceptable salt thereof according to any of the preceding aspects of the general formula $XZ_n$-Ins-$Z^1_m X^1$, wherein
  a. Ins represents an insulin comprising a B29 lysine residue,
  b. X and $X^1$ is a fatty diacid substitution, and X is located at said B29 lysine residue and $X^1$ is located at said N-terminal of the A chain and wherein X and $X^1$ consist of 20 carbon atoms
  c. Z and $Z^1$ is a linker between Ins and X and $X^1$ respectively, and wherein Z and $Z^1$ are gGlu-OEG-OEG
  d. n and m is 1.

54) An insulin derivative or a pharmaceutically acceptable salt hereof according to any of the preceding claims, to the extent possible, selected from the group consisting of A22N$^\alpha$-hexadecandioyl-γ-L-glutamyl B29N$^\epsilon$-hexadecandioyl-γ-L-glutamyl A22K desB30 human insulin, A22N$^\epsilon$-octadecandioyl-γ-L-glutamyl-OEG-OEG B29N$^\epsilon$-octadecandioyl-γ-L-glutamyl-OEG-OEG A22K desB30 human insulin, A22N$^\epsilon$-tetradecandioyl-γ-L-glutamyl B29N$^\epsilon$-tetradecandioyl-γ-L-glutamyl A22K desB30 human insulin, A22N$^\epsilon$-octadecandioyl-γ-D-glutamyl B29N$^\epsilon$-octadecandioyl-γ-D-glutamyl A22K desB30 human insulin, A22N$^\epsilon$-hexadecandioyl-γ-L-glutamyl B29N$^\epsilon$-hexadecandioyl-γ-L-glutamyl A14E A22K B25H desB30 human insulin, A22N$^\epsilon$-octadecandioyl-γ-L-glutamyl-OEG-OEG B29N$^\epsilon$-octadecandioyl-γ-L-glutamyl-OEG-OEG A14E A22K B25H desB30 human insulin, A1N$^\alpha$-hexadecandioyl-γ-L-glutamyl B29N$^\epsilon$-hexadecandioyl-γ-L-glutamyl A14E B25H desB30 human insulin, A1N^α-hexadecandioyl-γ-L-glutamyl B29N^ε-hexadecandioyl-γ-L-glutamyl desB30 human insulin, A1N^α-octadecandioyl-γ-L-glutamyl-OEG-OEG B29N^ε-octadecandioyl-γ-L-glutamyl-OEG-OEG A14E B25H desB30 human insulin, A1N^α-octadecandioyl-γ-L-glutamyl-OEG-OEG-aminomethyl-benzyl B1N^α-octadecandioyl-γ-L-glutamyl-OEG-OEG-4-aminomethyl-benzyl A14E B25H desB27 desB30 human insulin, A1N^α-octadecandioyl-γ-L-glutamyl-OEG-OEG-aminomethyl-benzyl B1N^α-octadecandioyl-γ-L-glutamyl-OEG-OEG-4-aminomethyl-benzyl A14E B25H desB30 human insulin, A1N^α-hexadecandioyl-γ-L-glutamyl-OEG-OEG-aminomethyl-benzyl B1N^α-hexadecandioyl-γ-L-glutamyl-OEG-OEG-4-aminomethyl-benzyl A14E B25H desB27 desB30 human insulin, A1N^α-tetradecandioyl-γ-L-glutamyl-OEG-OEG-aminomethyl-benzyl B1N^α-tetradecandioyl-γ-L-glutamyl-OEG-OEG-4-aminomethyl-benzyl A14E B25H desB27 desB30 human insulin, A1N^α-hexadecandioyl-γ-L-glutamyl-OEG-OEG4-aminomethyl-benzyl B1N^α-hexadecandioyl-γ-L-glutamyl-OEG-OEG-4-aminomethyl-benzyl A14E B25H desB30 human insulin, B1N^α-octadecandioyl-γ-L-glutamyl-OEG-OEG-aminomethyl-benzyl B29N^ε-octadecandioyl-γ-L-glutamyl-OEG-OEG A14E B25H desB30 human insulin, A1N^α-octadecandioyl-γ-L-glutamyl-OEG-OEG-4-aminomethyl-benzyl B1N^α-octadecandioyl-γ-L-glutamyl-OEG-OEG-4-aminomethyl-benzyl B29N^ε octadecandioyl-γ-L-glutamyl-OEG-OEG A14E B25H desB30 human insulin, A1N^α-octadecandioyl-N-carboxymethyl-beta-alanyl B29N^ε-octadecandioyl-N-carboxymethyl-beta-alanyl A14E B25H desB30 human insulin, A1N^α octadecandioyl-N-2-carboxyethyl-glycyl B29N^ε-octadecandioyl-N-2-carboxyethyl-glycyl A14E B25H desB30 human insulin, A1N^α-octadecandioyl-N-carboxymethyl-beta-alanyl A22N^ε-N-octadecandioyl-N-carboxymethyl-beta-alanyl A22K B29R desB30 human insulin, A22N^ε-hexadecandioyl-γ-L-glutamyl-OEG-OEG B29N^ε-hexadecandioyl-γ-L-glutamyl-OEG-OEG A14E B25H desB30 human insulin, A1N^α-hexadecandioyl-γ-L-glutamyl-OEG-OEG B29N^ε-hexadecandioyl-γ-L-glutamyl-OEG-OEG A14E B25H desB30 human insulin, A1N^α-hexadecandioyl-γ-L-glutamyl-OEG-OEG B29N^ε-hexadecandioyl-γ-L-glutamyl-OEG-OEG A14E B16H B25H desB30 human insulin, A1N^α-octadecandioyl-γ-L-glutamyl-OEG-OEG B1N^α-octadecandioyl-γ-L-glutamyl-OEG-OEG A14E B25H B29R desB30 human, A22N^ε-eicosandioyl-γ-L-glutamyl-OEG-OEG B29N^ε-eicosandioyl-γ-L-glutamyl-OEG-OEG A14E A22K B25H desB30 human insulin, B1N^α-octadecandioyl-γ-L-glutamyl-OEG-OEG-4-aminomethyl-benzyl B29N^ε-octadecandioyl-γ-L-glutamyl-OEG-OEG A14E B16H B25H desB30 human insulin, B1N^α-(octadecandioyl-γ-L-glutamyl-OEG-OEG-4-aminomethyl-benzyl A14E B25H B29N^ε-octadecandioyl-γ-L-glutamyl-OEG-OEG desB30 human insulin, B1N^α-octadecandioyl-γ-L-glutamyl-OEG-OEG-aminomethyl-benzyl B29N^ε-octadecandioyl-γ-L-glutamyl-OEG-OEG A14E B25H desB27 desB30 human insulin, A22N^ε-4-carboxyphenoxy-decanoyl-γ-L-glutamyl-OEG-OEG B29N^ε-4-carboxyphenoxy-decanoyl-γ-L-glutamyl-OEG-OEG A14E A22K B25H desB30 human insulin.

55) An insulin derivative or a pharmaceutically acceptable salt thereof according to any of the preceding aspects, for the use as a pharmaceutical.

56) An insulin derivative according to any of the preceding claims, wherein said insulin derivative is soluble in aqueous solution.

57) A soluble insulin derivative or a pharmaceutically acceptable salt thereof of the general formula

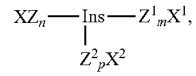

wherein a. Ins represents an insulin comprising a B29 lysine or B29 arginine residue and/or a A22 lysine residue b. X, $X^1$ and $X^2$ is a fatty diacid substitution and $X^2$ is optional, wherein said fatty diacid substitution comprises 14-20 carbon atoms c. Z, $Z^1$ and $Z^2$ is a linker between Ins and X, $X^1$ and $X^2$, respectively and d. n, m and p is zero or 1.

58) A soluble insulin derivative or a pharmaceutically acceptable salt thereof of the general formula

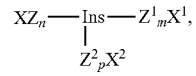

wherein a. Ins represents an insulin comprising a B29 lysine or B29 arginine residue and/or a A22 lysine residue b. X, $X^1$ and $X^2$ is a fatty diacid substitution and $X^2$ is optional, wherein said fatty diacid substitution comprises 14-20 carbon atoms c. Z, $Z^1$ and $Z^2$ is a linker between Ins and X, $X^1$ and $X^2$, respectively and d. n, m and p is zero or 1.

59) A soluble insulin derivative or a pharmaceutically acceptable salt thereof of the general formula

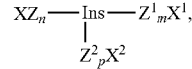

wherein a. Ins represents an insulin comprising a B29 lysine or B29 arginine residue and/or a A22 lysine residue b. X, $X^1$ and $X^2$ is a fatty diacid substitution and $X^2$ is optional, wherein said fatty diacid substitution comprises 14-20 carbon atoms c. Z, $Z^1$ and $Z^2$ is a linker between Ins and X, $X^1$ and $X^2$, respectively and d. n, m and p is zero or 1.

60) The soluble insulin derivative or pharmaceutically acceptable salt according to claim 1 for use as a pharmaceutical.

61) The soluble insulin derivative or pharmaceutically acceptable salt thereof according to any of the preceding claims of the general formula

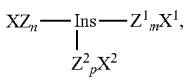

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: B29 lysine, A22 lysine, N-terminal of the A chain, N-terminal of the B-chain, wherein said fatty diacid substitution comprises 14-20 carbon atoms
  c. Z, $Z^1$ and $Z^2$ is a linker between Ins and X, $X^1$ and $X^2$, respectively and
  d. n, m and p is zero or 1.

62) The soluble insulin derivative or pharmaceutically acceptable salt thereof according to any of the preceding claims of the general formula

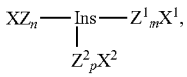

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: A22 lysine, N-terminal of the A chain, N-terminal of the B-chain, wherein said fatty diacid substitution comprises 14-20 carbon atoms
  c. Z, $Z^1$ and $Z^2$ is a linker between Ins and X, $X^1$ and $X^2$, respectively and
  d. n, m and p is zero or 1.

63) The soluble insulin derivative or pharmaceutically acceptable salt thereof according to any of the preceding claims of the general formula

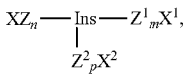

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: B29 lysine, A22 lysine, N-terminal of the B-chain, wherein said fatty diacid substitution comprises 14-20 carbon atoms
  c. Z, $Z^1$ and $Z^2$ is a linker between Ins and X, $X^1$ and $X^2$, respectively and
  d. n, m and p is zero or 1.

64) The soluble insulin derivative or pharmaceutically acceptable salt thereof according to any of the preceding claims of the general formula $XZ_n$-Ins-$Z^1_m X^1$, wherein
  a. Ins represents an insulin comprising a B29 lysine or B29 arginine residue and/or a A22 lysine residue,
  b. X and $X^1$ is a fatty diacid substitution, wherein said fatty diacid substitution comprises 14-20 carbon atoms
  c. Z and $Z^1$ is a linker between Ins and X and $X^1$ respectively, and
  d. n and m is zero or 1.

65) The soluble insulin derivative or pharmaceutically acceptable salt thereof according to any of the preceding claims of the general formula $XZ_n$-Ins-$Z^1_m X^1$, wherein
  a. Ins represents an insulin comprising a B29 lysine or B29 arginine residue and/or a A22 lysine residue,
  b. X and $X^1$ is a fatty diacid substitution and respectively located in a position selected from the group consisting of: B29 lysine, A22 lysine, N-terminal of the A chain, N-terminal of the B-chain, wherein said fatty diacid substitution comprises 14-20 carbon atoms 66) The soluble insulin derivative or pharmaceutically acceptable salt thereof according to any of the preceding claims of the general formula

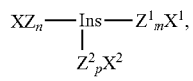

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: B29 lysine, A22 lysine, N-terminal of the A chain, N-terminal of the B-chain, wherein said fatty diacid substitution comprises 14, 16, 18 or 20 carbon atoms
  c. Z, $Z^1$ and $Z^2$ is a linker between Ins and X, $X^1$ and $X^2$, respectively and
  d. n, m and p is zero or 1.

67) The soluble insulin derivative or pharmaceutically acceptable salt thereof according to any of the preceding claims of the general formula

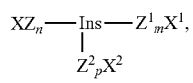

wherein
  a. Ins represents an insulin comprising a B29 lysine or B29 arginine residue and/or a A22 lysine residue,
  b. X, $X^1$ and $X^2$ is a fatty diacid substitution and respectively located in a position selected from the group consisting of: A22 lysine, N-terminal of the A chain, N-terminal of the B-chain, wherein said fatty diacid substitution comprises 14, 16, 18 or 20 carbon atoms
  c. Z, $Z^1$ and $Z^2$ is a linker between Ins and X, $X^1$ and $X^2$, respectively and
  d. n, m and p is zero or 1.

68) The soluble insulin derivative or pharmaceutically acceptable salt thereof according to any of the preceding claims of the general formula

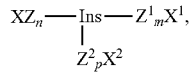

wherein
  a. Ins represents an insulin comprising a B29 lysine or B29 arginine residue and/or a A22 lysine residue,
  b. X, $X^1$ and $X^2$ is a fatty diacid substitution and respectively located in a position consisting of: B29 lysine, A22 lysine, N-terminal of the B-chain, wherein said fatty diacid substitution comprises 14, 16, 18 or 20 carbon atoms
c. Z, $Z^1$ and $Z^2$ is a linker between Ins and X, $X^1$ and $X^2$, respectively and
d. n, m and p is zero or 1.

69) The soluble insulin derivative or pharmaceutically acceptable salt thereof according to any of the preceding claims of the general formula $XZ_n$-Ins-$Z^1{}_m X^1$, wherein
a. Ins represents an insulin comprising a B29 lysine or B29 arginine residue and/or a A22 lysine residue,
b. X and $X^1$ is a fatty diacid substitution, wherein said fatty diacid substitution comprises 14, 16, 18 or 20 carbon atoms
c. Z and $Z^1$ is a linker between Ins and X and $X^1$ respectively, and
d. n and m is zero or 1.

70) The soluble insulin derivative or pharmaceutically acceptable salt thereof according to any of the preceding claims of the general formula $XZ_n$-Ins-$Z^1{}_m X^1$, wherein
a. Ins represents an insulin comprising a B29 lysine or B29 arginine residue and/or a A22 lysine residue,
b. X and $X^1$ is a fatty diacid substitution and respectively located in a position selected from the group consisting of: B29 lysine, A22 lysine, N-terminal of the A chain, N-terminal of the B-chain, wherein said fatty diacid substitution comprises 14, 16, 18 or 20 carbon atoms
c. Z and $Z^1$ is a linker between Ins and X and $X^1$ respectively, and
d. n and m is zero or 1.

71) The soluble insulin derivative or pharmaceutically acceptable salt thereof according to any of the preceding claims, wherein said fatty acid substitutions are selected from a group of protracting moieties selected from Chem. 1 and Chem. 2:

HOOC—(CH$_2$)$_x$—CO—*    Chem 1

HOOC—C$_6$H$_4$—O—(CH$_2$)$_y$—CO—*    Chem 2

Wherein x is an integer from 10 to 20 and y is an integer from 6 to 14.

72) The soluble insulin derivative or pharmaceutically acceptable salt thereof according to any of the preceding claims, wherein said fatty acid substitutions are selected from a group of protracting moieties selected from Chem. 1 and Chem. 2:

HOOC—(CH$_2$)$_x$—CO—*    Chem 1

HOOC—C$_6$H$_4$—O—(CH$_2$)$_y$—CO—*    Chem 2

Wherein x is 14, 16 or 18 and y is 8, 10 or 12.

73) The soluble insulin derivative or pharmaceutically acceptable salt thereof according to any of the preceding claims, wherein said fatty diacid substitution is attached at an amino acid residue in said insulin, in a position selected from the group consisting of A1, A22, B1 and B29.

74) The soluble insulin derivative or pharmaceutically acceptable salt thereof according to any of the preceding claims, wherein said fatty diacid substitutions are attached to amino acid residues of the insulin via a linker.

75) The soluble insulin derivative or pharmaceutically acceptable salt thereof according to any of the preceding claims, wherein said linker comprises one or more linker elements selected from the group consisting of: alpha-L-Glu, alpha-D-Glu, gamma-L-Glu, gamma-D-Glu, alpha-L-Asp, alpha-D-Asp, beta-L-Asp, beta-D-Asp, CPH, IDA and OEG.

76) The soluble insulin derivative or pharmaceutically acceptable salt thereof according to any of the preceding claims for the use as a medicament in the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

77) The soluble insulin derivative or pharmaceutically acceptable salt hereof according to any of the preceding claims, selected from the group consisting of A22N$^\alpha$-hexadecandioyl-γ-L-glutamyl B29N$^\epsilon$-hexadecandioyl-γ-L-glutamyl A22K desB30 human insulin, A22N$^\epsilon$-octadecandioyl-γ-L-glutamyl-OEG-OEG B29N$^\epsilon$-octadecandioyl-γ-L-glutamyl-OEG-OEG A22K desB30 human insulin, A22N$^\epsilon$-tetradecandioyl-γ-L-glutamyl B29N$^\epsilon$-tetradecandioyl-γ-L-glutamyl A22K desB30 human insulin, A22N$^\epsilon$-octadecandioyl-γ-D-glutamyl B29N$^\epsilon$-octadecandioyl-γ-D-glutamyl A22K desB30 human insulin, A22N$^\epsilon$-hexadecandioyl-γ-L-glutamyl B29N$^\epsilon$-hexadecandioyl-γ-L-glutamyl A14E A22K B25H desB30 human insulin, A22N$^\epsilon$-octadecandioyl-γ-L-glutamyl-OEG-OEG B29N$^\epsilon$-octadecandioyl-γ-L-glutamyl-OEG-OEG A14E A22K B25H desB30 human insulin, A1N$^\alpha$-hexadecandioyl-γ-L-glutamyl B29N$^\epsilon$-hexadecandioyl-γ-L-glutamyl A14E B25H desB30 human insulin, A1N$^\alpha$-hexadecandioyl-γ-L-glutamyl B29N$^\epsilon$-hexadecandioyl-γ-L-glutamyl desB30 human insulin, A1N$^\alpha$-octadecandioyl-γ-L-glutamyl-OEG-OEG B29N$^\epsilon$-octadecandioyl-γ-L-glutamyl-OEG-OEG A14E B25H desB30 human insulin, A1N$^\alpha$-octadecandioyl-γ-L-glutamyl-OEG-OEG-aminomethyl-benzyl B1N$^\alpha$-octadecandioyl-γ-L-glutamyl-OEG-OEG-4-aminomethyl-benzyl A14E B25H desB27 desB30 human insulin, A1N$^\alpha$-octadecandioyl-γ-L-glutamyl-OEG-OEG-aminomethyl-benzyl B1N$^\alpha$-octadecandioyl-γ-L-glutamyl-OEG-OEG-4-aminomethyl-benzyl A14E B25H desB30 human insulin, A1N$^\alpha$-hexadecandioyl-γ-L-glutamyl-OEG-OEG-aminomethyl-benzyl B1N$^\alpha$-hexadecandioyl-γ-L-glutamyl-OEG-OEG-4-aminomethyl-benzyl A14E B25H desB27 desB30 human insulin, A1N$^\alpha$-tetradecandioyl-γ-L-glutamyl-OEG-OEG-aminomethyl-benzyl B1N$^\alpha$-tetradecandioyl-γ-L-glutamyl-OEG-OEG-4-aminomethyl-benzyl A14E B25H desB27 desB30 human insulin, A1N$^\alpha$-hexadecandioyl-γ-L-glutamyl-OEG-OEG4-aminomethyl-benzyl B1N$^\alpha$-hexadecandioyl-γ-L-glutamyl-OEG-OEG-4-aminomethyl-benzyl A14E B25H desB30 human insulin, B1N$^\alpha$-octadecandioyl-γ-L-glutamyl-OEG-OEG-aminomethyl-benzyl B29N$^\epsilon$-octadecandioyl-γ-L-glutamyl-OEG-OEG A14E B25H desB30 human insulin, A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl B29N$^\epsilon$octadecandioyl-γ-L-glutamyl-OEG-OEG A14E B25H desB30 human insulin, A1N$^\alpha$-octadecandioyl-N-carboxymethyl-beta-alanyl B29N$^\epsilon$-octadecandioyl-N-carboxymethyl-beta-alanyl A14E B25H desB30 human insulin, A1N$^\alpha$octadecandioyl-N-2-carboxyethyl-glycyl B29N$^\epsilon$-octadecandioyl-N-2-carboxyethyl-glycyl A14E B25H desB30 human insulin, A1N$^\alpha$-octadecandioyl-N-carboxymethyl-beta-alanyl A22N$^\epsilon$-N-octadecandioyl-N-carboxymethyl-beta-alanyl A22K B29R desB30 human insulin, A22N$^\epsilon$-hexadecandioyl-γ-L-glutamyl-OEG-OEG B29N$^\epsilon$-hexadecandioyl-γ-L-glutamyl-OEG-OEG A14E B25H desB30 human insulin, A1N$^\alpha$-hexadecandioyl-γ-L-glutamyl-OEG-OEG B29N$^\epsilon$-hexadecandioyl-γ-L-glutamyl-OEG-OEG A14E B25H desB30 human insulin, A1N$^\alpha$-hexadecandioyl-γ-L-glutamyl-OEG-OEG B29N$^\epsilon$-hexadecandioyl-γ-L-glutamyl-OEG-OEG A14E B16H B25H desB30 human insulin, A1N$^\alpha$-octadecandioyl-γ-L-glutamyl-OEG-OEG B1N$^\alpha$-octadecandioyl-γ-L-glutamyl-OEG-OEG A14E B25H B29R desB30 human, A22N$^\epsilon$-eicosandioyl-γ-L-glutamyl-OEG-OEG B29N$^\epsilon$-eicosandioyl-γ-L-glutamyl-OEG-OEG A14E A22K B25H desB30 human insulin, B1N$^\alpha$-octadecandioyl-γ-L-glutamyl-OEG-OEG-4-aminomethyl-benzyl B29N$^\epsilon$-octadecandioyl-γ-L-glutamyl-OEG-OEG A14E B16H B25H desB30 human insulin, B1N$^\alpha$-(octadecandioyl-γ-L-glutamyl-OEG-OEG-4-aminomethyl-benzyl A14E B25H B29N$^\epsilon$-octadecandioyl-γ-L-glutamyl-OEG-OEG desB30 human insulin, B1N$^\alpha$-octadecandioyl-γ-L-glutamyl-OEG-OEG-aminomethyl-benzyl B29N$^\epsilon$-octadecandioyl-γ-L-glutamyl-OEG-OEG A14E B25H desB27 desB30 human insulin, A22N$^\epsilon$-4-carboxyphenoxy-decanoyl-γ-L-glutamyl-OEG-OEG B29N$^\epsilon$-4-carboxyphenoxy-decanoyl-γ-L-glutamyl-OEG-OEG A14E A22K B25H desB30 human insulin.
78) A method for preparing an insulin derivative according to any of the above claims comprising either a step of acylation or alkylation
79) A method for preparing an insulin derivative according to any of the above aspects.
80) A method for preparing an insulin derivative according to any of the above aspects by reductive alkylation and/or acylation of an insulin.
81) A method for preparing an insulin derivative according to any of the above aspects by reductive alkylation of an insulin.
82) A method for preparing an insulin derivative according to any of the above aspects by acylation of an insulin.
83) Use of an insulin derivative or a pharmaceutically acceptable salt thereof according to the aspects 1-77 as a medicament.
84) Use of an insulin derivative or a pharmaceutically acceptable salt thereof according to the aspects 1-77 for the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.
85) An insulin derivative or a pharmaceutically acceptable salt thereof according to any of the aspects 1-77, wherein said fatty diacid substitution X is located in the position B29 lysine and fatty diacid substitution X$^1$ is located at the N-terminal of the A chain of said insulin, wherein X and X$^1$ consist of 20 carbon atoms and said linkers Z and Z$^1$ are gGlu-OEG-OEG.
86) Use of an insulin derivative or a pharmaceutically acceptable salt thereof according to any of the aspects 1-77, wherein said fatty diacid substitution X is located in the position B29 lysine and fatty diacid substitution X$^1$ is located at the N-terminal of the A chain of said insulin, wherein X and X$^1$ consist of 20 carbon atoms and said linkers Z and Z$^1$ are gGlu-OEG-OEG as a medicament.
87) Use of an insulin derivative or a pharmaceutically acceptable salt thereof according to any of the aspects 1-77, wherein said fatty diacid substitution X is located in the position B29 lysine and fatty diacid substitution X$^1$ is located at the N-terminal of the A chain of said insulin, wherein X and X$^1$ consist of 20 carbon atoms and said linkers Z and Z$^1$ are gGlu-OEG-OEG for the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.
88) An insulin derivative or a pharmaceutically acceptable salt thereof according to any of the aspects 1-77, wherein said fatty diacid substitution X is located in the position B29 lysine and fatty diacid substitution X$^1$ is located at the N-terminal of the A chain of said insulin, wherein X and X$^1$ consist of 20 carbon atoms and said linkers Z and Z$^1$ are not gGlu-OEG-OEG.
89) An insulin derivative or a pharmaceutically acceptable salt thereof according to any of the aspects 1-77, wherein said fatty diacid substitution X is located in the position B29 lysine and fatty diacid substitution X$^1$ is located at the N-terminal of the A chain of said insulin, and wherein said linkers Z and Z$^1$ are gGlu-OEG-OEG and said wherein X and X$^1$ do not consist of 20 carbon atoms.
90) An insulin derivative or a pharmaceutically acceptable salt thereof according to any of the aspects 1-77, wherein if said fatty diacid substitution X is located in the position B29 lysine and fatty diacid substitution X$^1$ is located at the N-terminal of the A chain of said insulin, and wherein said linkers Z and Z$^1$ are gGlu-OEG-OEG, then said wherein X and X$^1$ do not consist of 20 carbon atoms.
91) An insulin derivative or a pharmaceutically acceptable salt thereof according to any of the aspects 1-72, wherein if said fatty diacid substitution X is located in the position B29 lysine and fatty diacid substitution X$^1$ is located at the N-terminal of the A chain of said insulin, wherein X and X$^1$ consist of 20 carbon atoms and then said linkers Z and Z$^1$ are not gGlu-OEG-OEG

LIST OF ABBREVIATIONS

AcOH, acetic acid
Cpm, counts per minute
Da, dalton
DCM, dichloromethane
DIPEA, N,N-diisopropylethylamine
DMSO, dimethylsulfoxide
EDTA, ethylenediamine tetraacetic acid
ESI, Electrospray ionization
Fmoc, Fluorenylmethyloxycarbonyl
HCCA, 4-hydroxy-α-cyano-cinnamic acid
HEPES, 4-(2-hydroxyethyl)-1-piperazineethanesulfonic acid
HPCD, 2-hydroxypropyl-beta-cyclodextrin
HPLC, High-performance liquid chromatography, sometimes referred to as high-pressure liquid chromatography
HSA, human serum albumin LC-MS/LCMS, Liquid chromatographymass spectrometry
IDDM, insulin dependent diabetes mellitus
IEF, Isoelectric focusing
NaAc, sodium acetate
NIDDM non-insulin dependent diabetes mellitus
NMP, N-methyl-pyrrolidone
MALDI, matrix-assisted laser disorbtion ionisation
MRT, Mean residence time
OEG, 8-amino-3,6-dioxaoctanoic acid, 8-amino-3,6-dioxaoctanoyl
RP-HPLC, Reversed phase HPLC
Rt, retention time
RT Room temperature
SPA, scintillation proximity assay
SPA-PVT, scintillation proximity assay polyvinyl toluene bead
T-boc, Di-tert-butyl dicarbonate
THF, tetrehydrofurane
TFA, trifluoroacetic acid
Tris, tris(hydroxymethyl)aminomethane
tRNA, transfer RNA
UV, ultraviolet

EXAMPLES

Example 1

A22N$^\alpha$-hexadecandioyl-γ-L-glutamyl B29N$^\epsilon$-hexadecandioyl-γ-L-glutamyl A22K desB30 human insulin

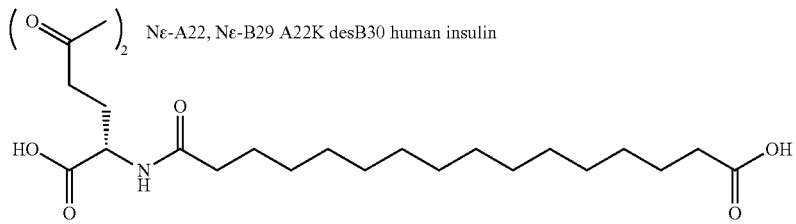

A22K desB30 insulin (200 mg, 34 μM) was dissolved in 0.2 M sodium carbonate, pH 10.5 (2.4 mL) and treated with hexadecandioyl-γ-succinimidyl-L-glutamate (44 mg, 86 uM, prepared as described in WO05012347) in acetonitrile (2.4 mL). pH was measured and adjusted to 10.5 if necessary. After 30 minutes, the reaction was quenched by addition of 0.2 M methylamine, pH 8 (0.24 mL). pH was adjusted to 5.5 using 1 M HCl and the precipitate was collected by centrifugation. The product was purified by RP-HPLC on C18 column using buffer A: 10 mM Tris, 15 mM ammonium sulfate, pH 7.3 in water/acetonitrile 80/20, buffer B: water/acetonitrile 20/80, gradient 11% B to 50% B over 60 minutes. The product was precipitated by adjustment of pH to 5.5 followed by centrifugation. Alternatively, the product was further purified by RP-HPLC on C18 column using buffer A: 0.1% trifluoroacetic acid in water, buffer B: 0.1% trifluoroacetic acid in acetonitrile, with product pools partially evaporated in vacuo and freeze-dried providing A22N$^\epsilon$-hexadecandioyl-γ-L-glutamyl B29N$^\epsilon$-hexadecandioyl-γ-L-glutamyl A22K desB30 human insulin.

Product LCMS: 1658.4 Da $[M+4H]^{4+}$.

Calculated for $C_{301}H_{458}N_{68}O_{88}S_6$ $[M+4H]^{4+}$: 1658.5 Da.

LCMS buffer A: 0.1% trifluoroacetic acid in water; buffer B: 0.1% trifluoroacetic acid in acetonitrile, gradient 10 to 90% B over 10 minutes.

Example 2

A22N$^\epsilon$-octadecandioyl-γ-L-glutamyl-OEG-OEG
B29N$^\epsilon$-octadecandioyl-γ-L-glutamyl-OEG-OEG
A22K desB30 human insulin

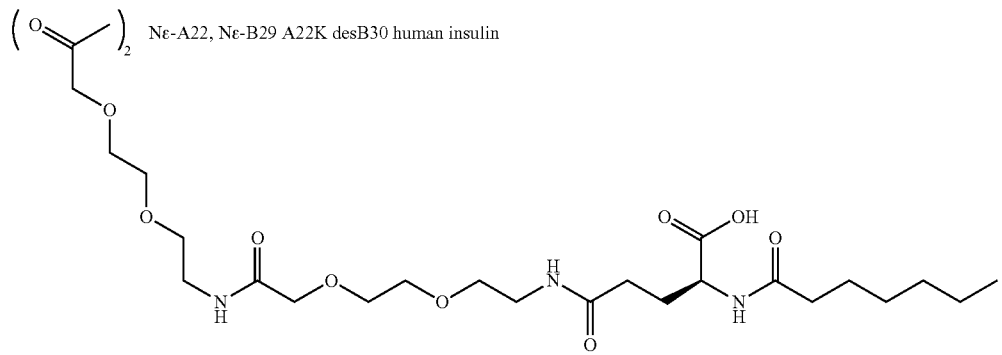

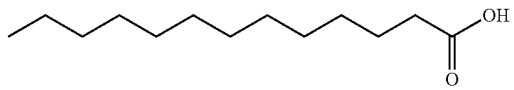

This compound was prepared in analogy with the compound of example 1 by using octadecandioyl-γ-L-glutamyl-OEG-OEG-succinimidyl as reagent, prepared as described in WO2010/029159.

Product LCMS: 1817.5 Da [M+4H]$^{4+}$.
Calculated for $C_{329}H_{510}N_{72}O_{100}S_6$ [M+4H]$^{4+}$: 1817.6 Da.

Example 3

A22N$^\epsilon$-tetradecandioyl-γ-L-glutamyl B29N$^\epsilon$-tetradecandioyl-γ-L-glutamyl A22K desB30 human insulin

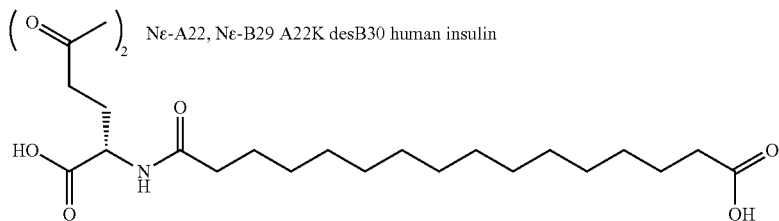

This compound was prepared in analogy with the compound of example 1 by using tetradecandioyl-γ-succinimidyl-L-glutamate as reagent.

Product LCMS: 1643.9 Da [M+4H]$^{4+}$.
Calculated for $C_{297}H_{450}N_{68}O_{88}S_6$ [M+4H]$^{4+}$: 1644.4 Da.

Example 4

A22N$^\epsilon$-octadecandioyl-γ-D-glutamyl B29N$^\epsilon$-octadecandioyl-γ-D-glutamyl A22K desB30 human insulin

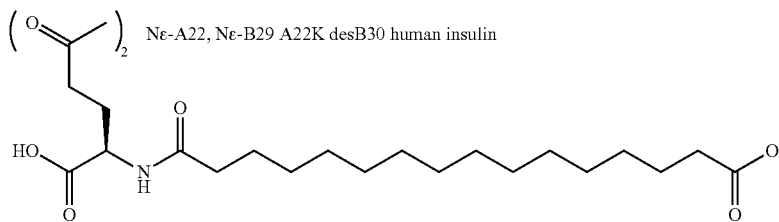

This compound was prepared in analogy with the compound of example 1 by using tert-butyl-octadecandioyl-γ-succinimidyl-D-glutamate-tert-butyl as reagent, prepared as described in WO05012347. The tert-butyl protecting groups were removed by treatment of the crude product with ice-cooled 95% trifluoroacetic acid/water for 45 minutes.

Product LCMS: 1672.2 Da [M+4H]$^{4+}$.
Calculated for $C_{305}H_{466}N_{68}O_{88}S_6$ [M+4H]$^{4+}$: 1672.5 Da.

Example 5

A22N$^\epsilon$-hexadecandioyl-γ-L-glutamyl B29N$^\epsilon$-hexadecandioyl-γ-L-glutamyl A14E A22K B25H desB30 human insulin

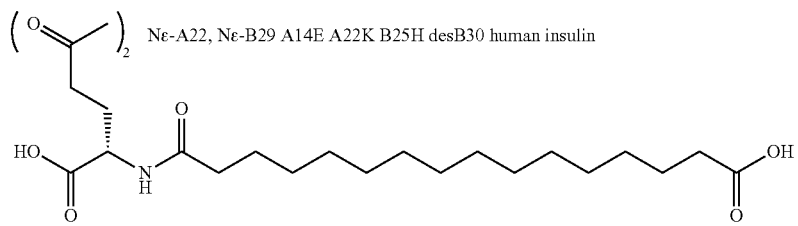

This compound was prepared in analogy with the compound of example 1 by using hexadecandioyl-γ-succinimidyl-L-glutamate and A14E A22K B25H desB30 human insulin.

Product LCMS: 1647.3 Da [M+4H]$^{4+}$.
Calculated for $C_{294}H_{454}N_{70}O_{89}S_6$ [M+4H]$^{4+}$: 1647.4 Da.

Example 6

A22N$^\epsilon$-octadecandioyl-γ-L-glutamyl-OEG-OEG B29N$^\epsilon$-octadecandioyl-γ-L-glutamyl-OEG-OEG A14E A22K B25H desB30 human insulin

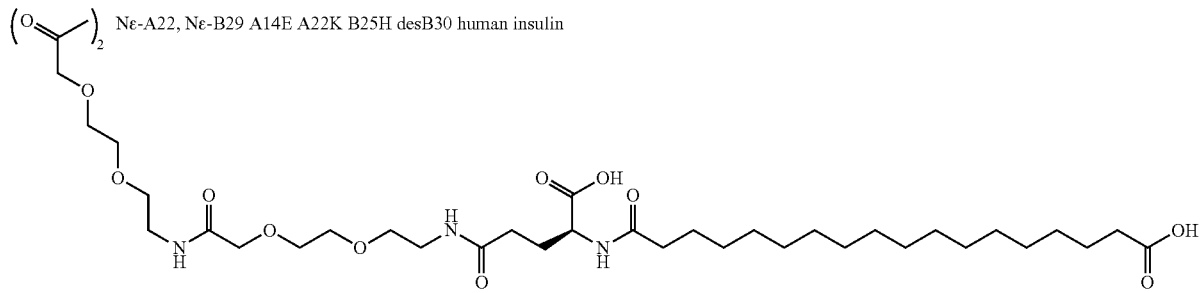

This compound was prepared in analogy with the compound of example 1 by using octadecandioyl-γ-L-glutamyl-OEG-OEG-succinimidyl and A14E A22K B25H desB30 human insulin.

Product LCMS: 1806.6 Da [M+4H]$^{4+}$.
Calculated for $C_{322}H_{506}N_{74}O_{101}S_6$ [M+4H]$^{4+}$: 1806.6 Da.

Example 7

A1N$^\alpha$-hexadecandioyl-γ-L-glutamyl B29N$^\epsilon$-hexadecandioyl-γ-L-glutamyl A14E B25H desB30 human insulin

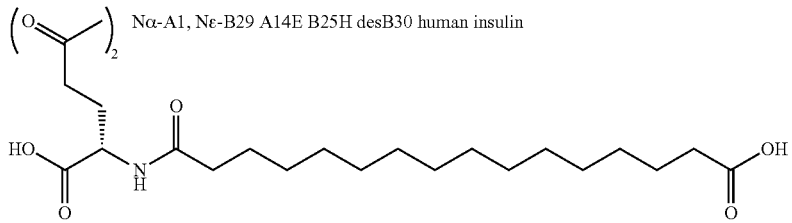

This compound was prepared in analogy with the compound of example 1 in 1:1 acetonitrile/0.2 M sodium carbonate, pH 9.0, by using hexadecandioyl-γ-succinimidyl-L-glutamate and A14E B25H desB30 human insulin.

Product LCMS: 1615.3 Da [M+4H]$^{4+}$.
Calculated for $C_{288}H_{442}N_{68}O_{88}S_6$ [M+4H]$^{4+}$: 1615.4 Da.

Affinity for HSA column, Rt (min): 8.0 minutes, the value for mono-substituted insulin C (see example 29 and table 1) 6.4 mins

Example 8

A1N$^\alpha$-hexadecandioyl-γ-L-glutamyl B29N$^\epsilon$-hexadecandioyl-γ-L-glutamyl desB30 human insulin

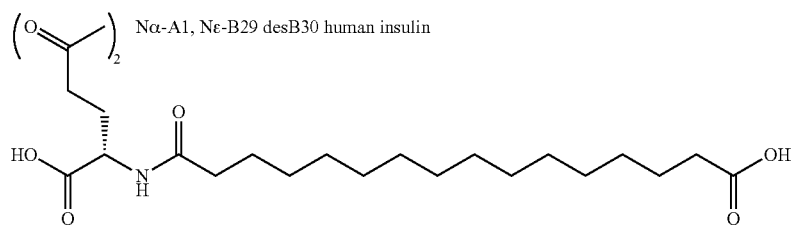

This compound was prepared in analogy with the compound of example 1 in 1:1 acetonitrile/0.2 M sodium carbonate, pH 9.0, by using hexadecandioyl-γ-succinimidyl-L-glutamate and desB30 human insulin.

Product LCMS: 1626.4 Da $[M+4H]^{4+}$.

Calculated for $C_{295}H_{446}N_{68}O_{87}S_6$ $[M+4H]^{4+}$: 1626.4 Da.

Example 9

A1N$^\alpha$-octadecandioyl-γ-L-glutamyl-OEG-OEG B29N$^\epsilon$-octadecandioyl-γ-L-glutamyl-OEG-OEG A14E B25H desB30 human insulin

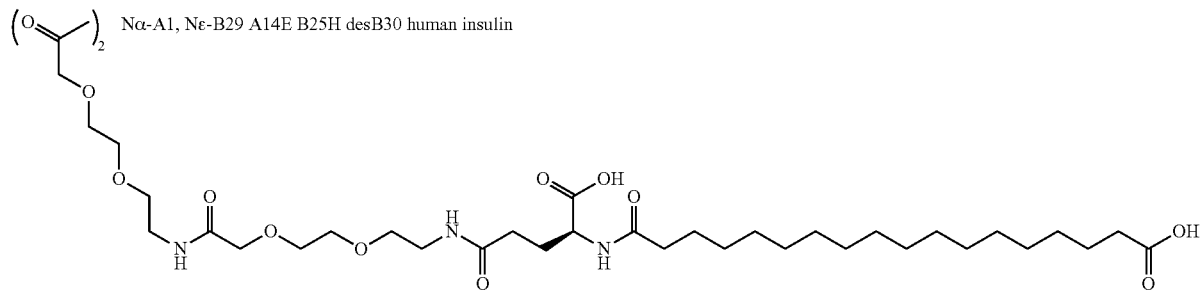

This compound was prepared in analogy with the compound of example 1 in 1:1 acetonitrile/0.2 M sodium carbonate, pH 9.0, by using octadecandioyl-γ-L-glutamyl-OEG-OEG-succinimidyl and A14E B25H desB30 human insulin.

Product LCMS: 1774.7 Da $[M+4H]^{4+}$.

Calculated for $C_{316}H_{494}N_{72}O_{100}S_6$ $[M+4H]^{4+}$: 1774.6 Da.

Example 10

A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB27 desB30 human insulin Preparation of octadecandioyl-γ-L-glutamyl-OEG-OEG-4-aminomethyl-benzaldehyde t-Butyl-N-(4-formylbenzyl)carbamate (100 mg) was treated with TFA/DCM (1:1) for 1 h. The mixture was concentrated in vacuo and co-concentrated with toluene twice. The residue was dissolved in THF (2.5 mL) and a solution of octadecandioyl-γ-L-glutamyl-OEG-OEG-succinimydyl ester (320 mg, prepared as described previously in WO2009/083549) in THF (5 mL) was added. DIPEA (0.5 mL) was added slowly. After 130 min, the mixture was concentrated in vacuo. The residue was dissolved in EtOAc and 1N HCl. The organic layer was extracted with 1N HCl and brine. The organic layer was dried ($Na_2SO_4$) and concentrated in vacuo to give the title compound as a white solid, which was used without further purification. Yield 234 mg (72%).

LCMS: Theoretical mass: 851.0 Found: 851.5 (M+1).

A zinc precipitate of A14E B25H desB27 desB30 human insulin corresponding to approximately 400 mg insulin was dissolved in water (32 mL) and EDTA (40 mg) was added. The mixture was left at RT or 1 h. pH was lowered to 4.8 with 10% AcOH. octadecandioyl-γ-L-glutamyl-OEG-OEG-4-aminomethyl-benzaldehyde (92 mg) dissolved in 1M NaAc (3.0 mL, heating under tap water) was added. After stirring for 10 min, 1M NaCNBH3 in water (0.715 mL) was added to give a 20 mM solution. Within a minute, the mixture became unclear and a sticky precipitate appeared. After 1 h more aldehyde (36 mg) and THF (3 mL) was added. After 40 minutes pH was lowered to 3.1 with AcOH and some Acetonitrile was added. The mixture was lyophilised. The product was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB27 desB30 human insulin

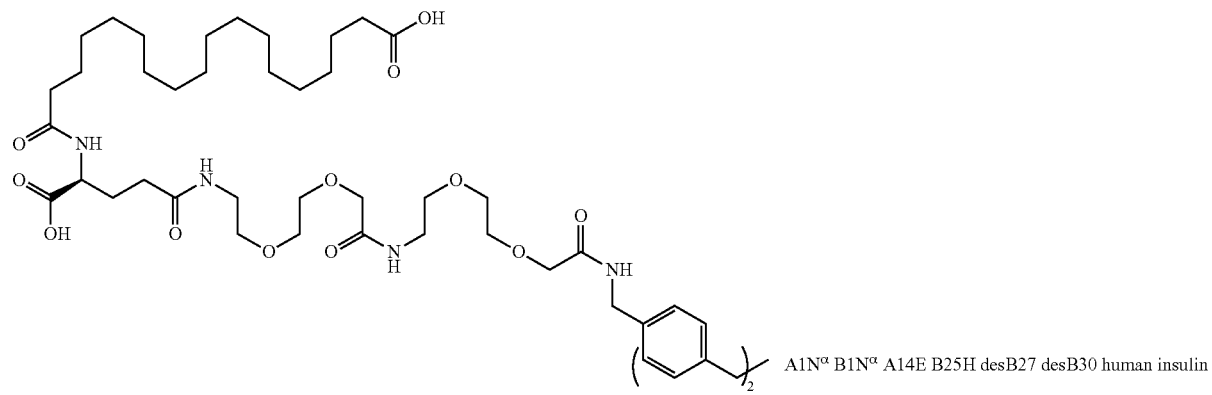

MALDI: (matrix, HCCA); m/z: 7233.5 Da, calculated for $C_{328}H_{505}N_{73}O_{98}S_6$: 7231.5 Da.

Example 11

A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB30 human insulin

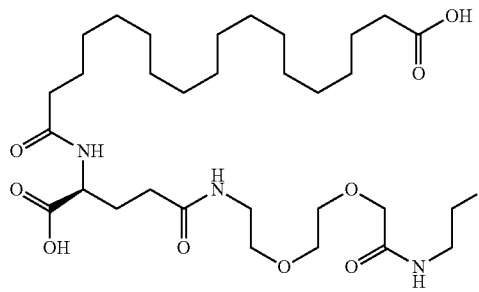

A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl A14E B25H desB30 human insulin MALDI: (matrix, HCCA); m/z: 7334.5 Da, calculated for $C_{332}H_{512}N_{74}O_{100}S_6$: 7332.6 Da.

Example 12

A1N$^\alpha$-hexadecandioyl-γ-L-glutamyl-OEG-OEG-aminomethyl-benzyl B1N$^\alpha$-hexadecandioyl-γ-L-glutamyl-OEG-OEG-4-aminomethyl-benzyl A14E B25H desB27 desB30 human insulin

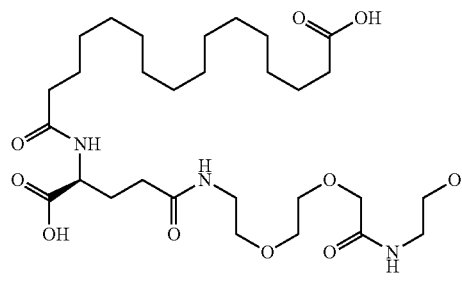

A14E B25H desB30 human insulin (300 mg) was dissolved in 1.0 M NaAc, pH 5.0 (3.2 mL). A solution of aldehyde octadecandioyl-γ-L-glutamyl-OEG-OEG-4-aminomethyl-benzaldehyde (79 mg) in 1.0 M NaAc, pH 5.0 (3.0 mL, heating under tap water) was added. The mixture gets unclear. After stirring for 5 minutes 1M NaCNBH$_3$ (135 μL) was added to give a 20 mM solution. pH is 4.9 and the reaction mixture appeared unclear. After 40 minutes pH was lowered to 3.1 with AcOH and some Acetonitrile was added. The mixture was lyophilised. The product was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing A zinc precipitate of A14E B25H desB27 desB30 human insulin corresponding to approximately 400 mg insulin was dissolved in water (48 mL) and EDTA (40 mg) was added. The mixture was left at RT for 45 min. pH was lowered to 5.0 with 10% AcOH. Hexadecandioyl-γ-L-glutamyl-OEG-OEG-4-aminomethyl-benzaldehyde (90 mg, prepared similarly octadecandioyl-γ-L-glutamyl-OEG-OEG-4-aminomethyl-benzaldehyde) dissolved in 1M NaAc (3.0 mL, heating under tap water) was added. After stirring for 7 min, 1M NaCNBH$_3$ in water (1.08 mL) was added to give a 20 mM solution. Within a minute, the mixture got unclear, after a while a sticky precipitate appeared. After 45 minutes pH was lowered to 3.1 with AcOH and some acetonitrile was added. The mixture was lyophilised. The product was purified by RP-HPLC on a C18 column using A: 0.1% trifluoroacetic acid in water, buffer B: 0.1% trifluoroacetic acid in acetonitrile. Gradient 20% B to 60% B over 45 minutes pH. Product pools were partially evaporated in vacuo and freeze-dried providing A1N$^\alpha$-Hexadecandioyl-γ-L-glutamyl-OEG-OEG-4-aminomethyl-benzyl B1N$^\alpha$-hexadecandioyl-γ-L-glutamyl-OEG-OEG-4-aminomethyl-benzyl A14E B25H desB27 desB30 human insulin MALDI: (matrix, HCCA); m/z: 7178.9 Da, Calculated for $C_{324}H_{497}N_{73}O_{98}S_6$: 7175.4 Da.

Example 13

A1N$^\alpha$-tetradecandioyl-γ-L-glutamyl-OEG-OEG-4-aminomethyl-benzyl B1N$^\alpha$-tetradecandioyl-γ-L-glutamyl-OEG-OEG-4-aminomethyl-benzyl A14E B25H desB27 desB30 human insulin

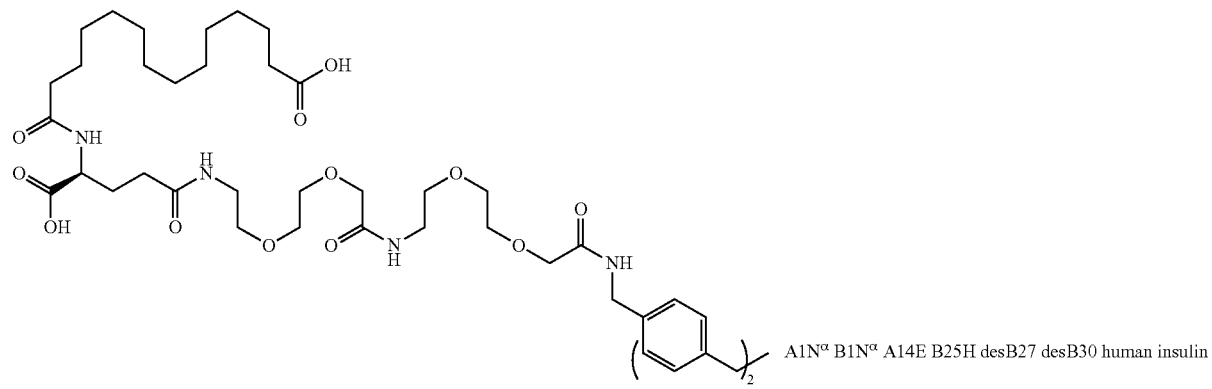

A zinc precipitate of A14E B25H desB27 desB30 human insulin corresponding to approximately 100 mg insulin was dissolved in water (16 mL) and EDTA (10 mg) was added. The mixture was left at RT for 1 h. pH was lowered to 4.8 with 10% AcOH. Tetradecandioyl-γ-L-glutamyl-OEG-OEG-4-aminomethyl-benzaldehyde (36 mg, prepared similarly as octadecandioyl-γ-L-glutamyl-OEG-OEG-4-aminomethyl-benzaldehyde) dissolved in 1M NaAc (0.75 mL, heating under tap water) was added. After stirring for 10 min, 1M NaCNBH$_3$ in water (0.35 mL) was added to give a 20 mM solution. Within a minute, the mixture got unclear after a while a sticky precipitate appeared. After 1 h more aldehyde (36 mg) and THF (3 mL) was added. After 4 h the mixture was stored at 5° C. over night. The product was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing A1N$^\alpha$-tetradecandioyl-γ-L-glutamyl-OEG-OEG-4-aminomethyl-benzyl B1N$^\alpha$-tetradecandioyl-γ-L-glutamyl-OEG-OEG-4-aminomethyl-benzyl A14E B25H desB27 desB30 human insulin LCMS: 1780.6 Da [M+4H]$^{4+}$. Calculated for $C_{320}H_{489}N_{73}O_{98}S_6$ [M+4H]$^{4+}$: 1780.8 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 7118.7 Da, calculated: 7119.3 Da.

Example 14

A1N$^\alpha$-hexadecandioyl-γ-L-glutamyl-OEG-OEG4-aminomethyl-benzyl B1N$^\alpha$-hexadecandioyl-γ-L-glutamyl-OEG-OEG-4-aminomethyl-benzyl A14E B25H desB30 human insulin

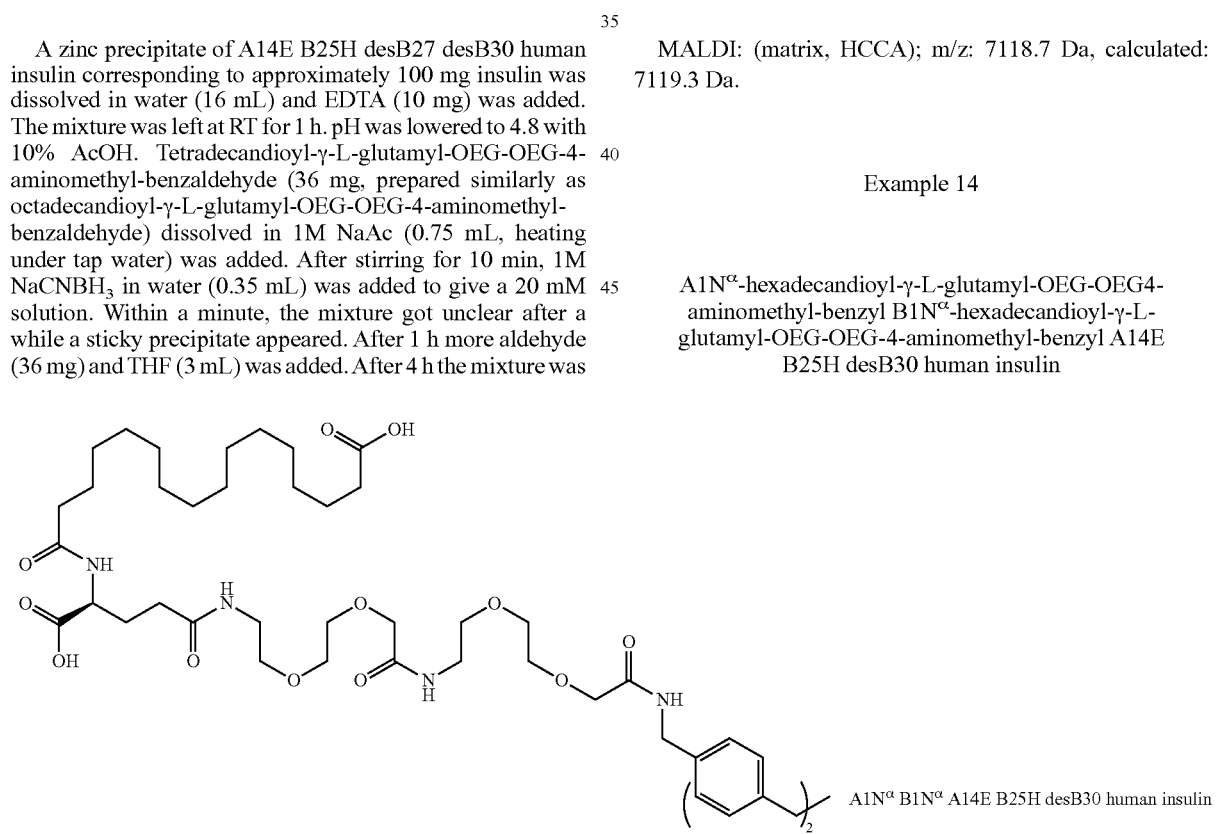

A14E B25H desB30 human insulin (300 mg) was dissolved in 1.0 M NaAc, pH 5.0 (3.2 mL). A solution of hexadecandioyl-γ-L-glutamyl-OEG-OEG-aminomethyl-benzaldehyde (79 mg) in 1.0 M NaAc, pH 5.0 (3.0 mL, heating under tap water) was added. The mixture gets unclear. After stirring for 5 minutes 1M $NaCNBH_3$ (135 μL) was added to give a 20 mM solution. pH is 4.9 and the reaction mixture is unclear but chaning. After 40 minutes pH was lowered to 3.1 with AcOH and some acetonitrile was added. The mixture was lyophilised. The product was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing A1N$^{\alpha}$-hexadecandioyl-γ-L-glutamyl-OEG-OEG-4-aminomethyl-benzyl B1N$^{\alpha}$-hexadecandioyl-γ-L-glutamyl-OEG-OEG-4-aminomethyl-benzyl A14E B25H desB30 human insulin MALDI: (matrix, HCCA); m/z: 7279.4 Da, calculated for $C_{328}H_{504}N_{74}O_{100}S_6$: 7276.5 Da.

Example 15

B1N$^{\alpha}$-octadecandioyl-γ-L-glutamyl-OEG-OEG-4-aminomethyl-benzyl B29N$^{\epsilon}$-octadecandioyl-γ-L-glutamyl-OEG-OEG A14E B25H desB30 human insulin B29N$^{\epsilon}$-octadecandioyl-γ-L-glutamyl-OEG-OEG A14E B25H desB30 human insulin, 300 mg, prepared as described in WO 2010/029159 was dissolved in 2M AcOH/NMP 9:1 (9 mL). pH was adjusted from 2.9 to 3.5 with 1N NaOH. Octadecandioyl-γ-L-glutamyl-OEG-OEG-4-aminomethyl-benzaldehyde (44 mg) in NMP (0.5 mL) was added. The mixture turned unclear, pH 3.77. After stirring for 15 minutes 1M 2-picoline borane complex in NMP/1M NaAc (0.45 mL) was added. pH is 3.77. The mixture was stirred at Rt. Sticky material gathered on top of the mixture. After 7 minutes the mixture was diluted with 1M AcOH (4.7 mL, to dilute the boride). After 1 h pH was lowered to 3.0 with AcOH to give a solution, which was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing B1N$^{\alpha}$-octadecandioyl-γ-L-glutamyl-OEG-OEG-4-aminomethyl-benzyl B29N$^{\epsilon}$-octadecandioyl-γ-L-glutamyl-OEG-OEG A14E B25H desB30 human insulin LCMS: 1804.8 Da $[M+4H]^{4+}$. Calculated for $C_{324}H_{503}N_{73}O_{100}S_6$ $[M+4H]^{4+}$: 1804.4 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 7215.9 Da, calculated for $C_{324}H_{503}N_{73}O_{100}S_6$: 7213.4 Da.

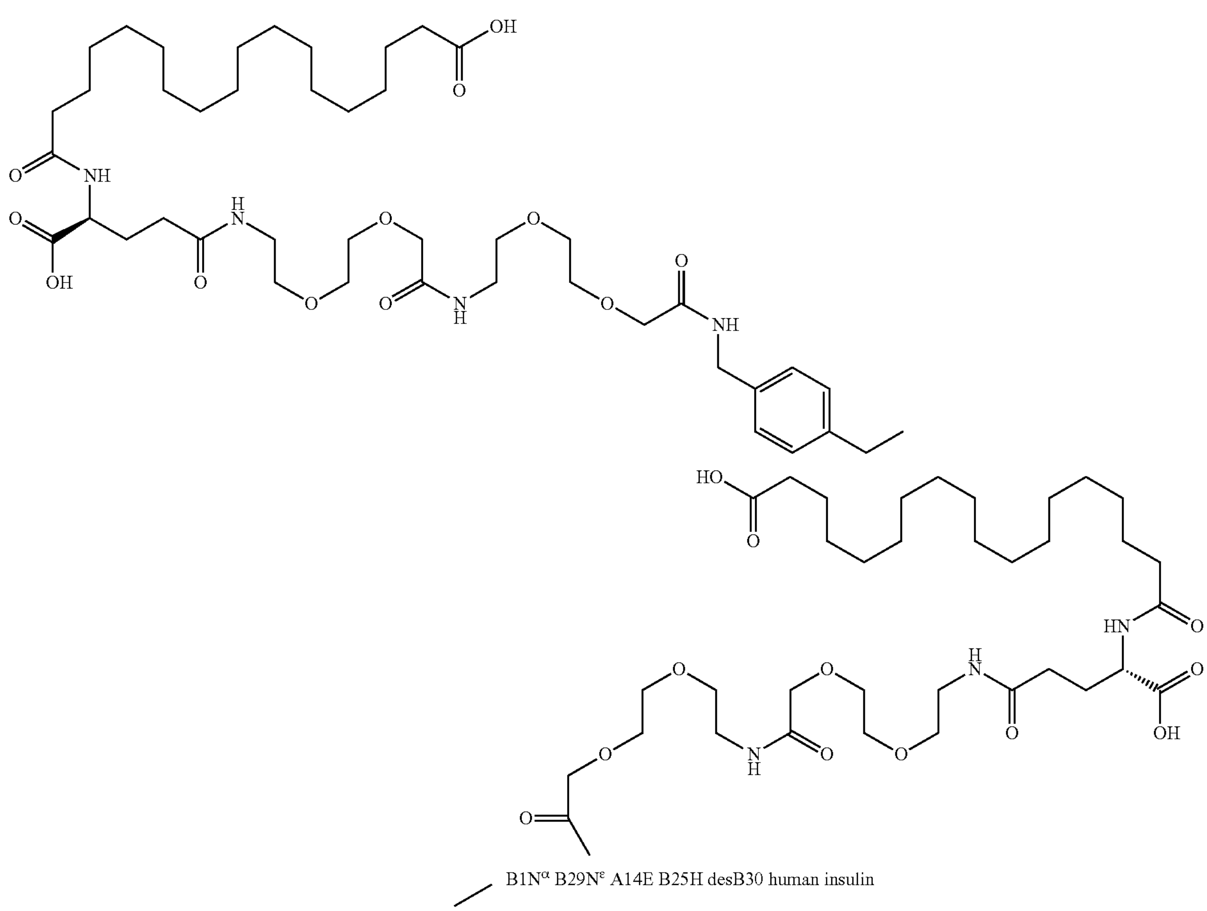

B1N$^{\alpha}$ B29N$^{\epsilon}$ A14E B25H desB30 human insulin

Example 16

A1N$^\alpha$-octadecandioyl-γ-L-glutamyl-OEG-OEG-4-aminomethyl-benzyl B1N$^\alpha$-octadecandioyl-γ-L-glutamyl-OEG-OEG-4-aminomethyl-benzyl B29N$^\epsilon$ octadecandioyl-γ-L-glutamyl-OEG-OEG A14E B25H desB30 human insulin

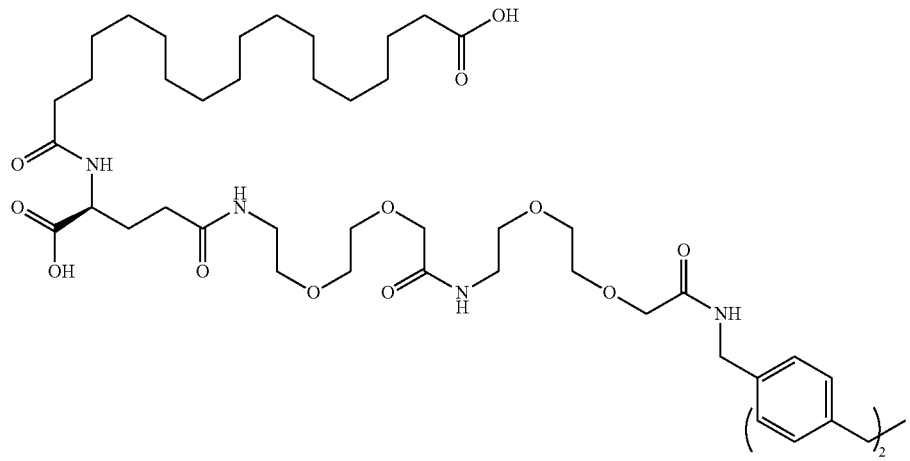

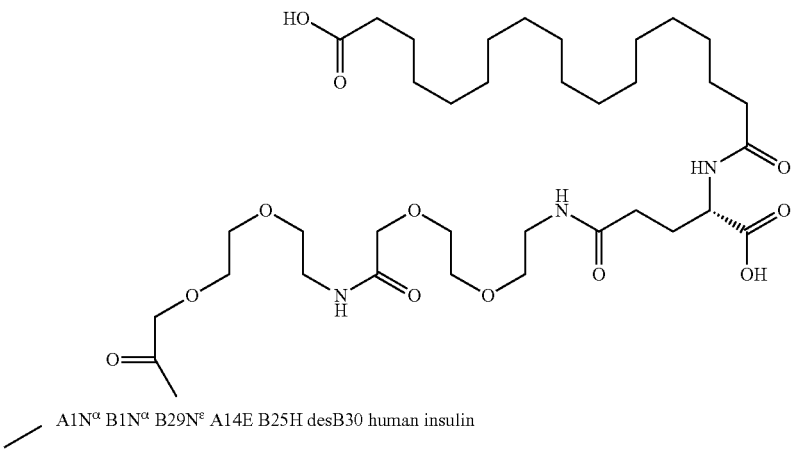

A1N$^\alpha$ B1N$^\alpha$ B29N$^\epsilon$ A14E B25H desB30 human insulin

B29N$^\epsilon$-octadecandioyl-γ-L-glutamyl-OEG-OEG A14E B25H desB30 human insulin (300 mg) was dissolved in 2 M AcOH/NMP 9:1 (9 mL). pH was adjusted from 2.9 to 3.5 with 1N NaOH, a sticky suspension was obtained. Octadecandioyl-γ-L-glutamyl-OEG-OEG-4-aminomethyl-benzaldehyde (44 mg) in NMP (0.5 mL) was added. The mixture turned unclear, pH is 3.77. After stirring for 15 minutes 1M 2-picoline borane complex in NMP/1M NaAc (0.45 mL) was added. pH is 3.77. The mixture was stirred at Rt. Sticky material gathered on top of the mixture. After 7 minutes the mixture was diluted with 1M AcOH (4.7 mL, to dilute the boride). After 1 h pH was lowered to 3.0 with AcOH to give a solution, which was purified by RP-HPLC on a C18 column using A: 0.1% trifluoroacetic acid in water, buffer B: 0.1% trifluoroacetic acid in acetonitrile. Gradient 20% B to 60% B over 45 minutes. Product pools were partially evaporated in vacuo and freeze-dried providing A1N$^\alpha$-octadecandioyl-γ-L-glutamyl-OEG-OEG-4-aminomethyl-benzyl B1N$^\alpha$-octadecandioyl-γ-L-glutamyl-OEG-OEG-aminomethyl-benzyl B29N$^\epsilon$-octadecandioyl-γ-L-glutamyl-OEG-OEG A14E B25H desB30 human insulin.

This example illustrates that a reaction of this type gives rise to B1 N-alkylation as main product.

LCMS: 1610.9 Da [M+5H]$^{5+}$. Calculated for $C_{367}H_{573}N_{77}O_{112}S_6$ [M+5H]$^{5+}$: 1610.7 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 8050.7 Da, calculated for $C_{367}H_{573}N_{77}O_{112}S_6$: 8048.5 Da.

Example 17

A1N$^{\alpha}$-octadecandioyl-N-carboxymethyl-beta-alanyl B29N$^{\epsilon}$-octadecandioyl-N-carboxymethyl-beta-alanyl A14E B25H desB30 human insulin

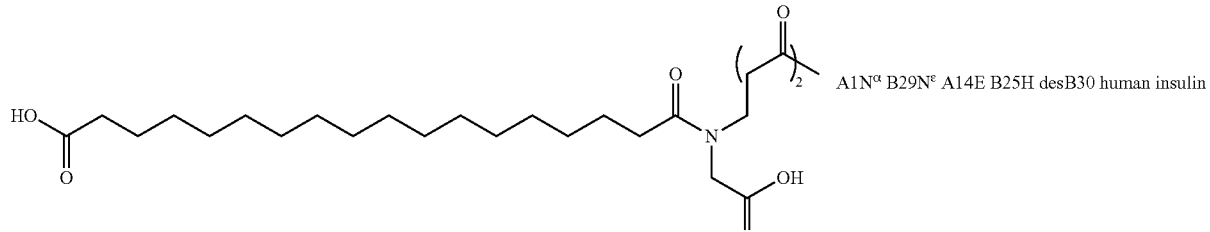

A14E B25H desB30 human insulin (200 mg) was dissolved in 100 mM aqueous Na$_2$CO$_3$ (4.5 mL), and pH adjusted to 10.1 with 1 N NaOH. tert-Butyl octadecandioyl-N-(tert-butoxycarbonylmethyl)-beta-alanyl-OSu (28 mg) (prepared as described in WO 2005/012347) was dissolved in THF (2.25 mL) and added to the insulin solution. Some precipitation was observed and more THF (0.75 mL) was added. Ph was 10.7. After 34 minutes more tert-butyl octadecandioyl-N-(tert-butoxycarbonylmethyl)-beta-alanyl-OSu (14 mg) was added. After 57 minutes water was added and pH was adjusted to 5.1 with 1N HCl. The precipitate was spinned down and lyophilised. The solid was dissolved in ice-cold 95% trifluoroacetic acid (containing 5% water) and kept on ice for 40 minutes. The mixture was concentrated in vacuo and re-evaporated from dichloromethane. The residue was purified by RP-HPLC on a C18 column using A: 0.1% trifluoroacetic acid in water, buffer B: 0.1% trifluoroacetic acid in acetonitrile. Gradient 20%1B to 55% B over 75 minutes. Product pools were partially evaporated in vacuo and freeze-dried providing A1N$^{\alpha}$-octadecandioyl-N-carboxymethyl-beta-alanyl B29N$^{\epsilon}$-octadecandioyl-N-carboxymethyl-beta-alanyl A14E B25H desB30 human insulin LCMS: 1629.0 Da [M+4H]$^{4+}$. Calculated for C$_{292}$H$_{450}$N$_{68}$O$_{88}$S$_6$ [M+4H]$^{4+}$: 1629.4 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 6511.0 Da, calculated for C$_{292}$H$_{450}$N$_{68}$O$_{88}$S$_6$: 6513.6 Da.

Example 18

A1N$^{\alpha}$octadecandioyl-N-2-carboxyethyl-glycyl B29N$^{\epsilon}$-octadecandioyl-N-2-carboxyethyl-glycyl A14E B25H desB30 human insulin A14E B25H desB30 human insulin (100 mg) was dissolved in DMSO (1.0 mL) and triethylamine (0.05 mL) was added. tert-Butyl octadecandioyl-N-(2-(tert-butoxycarbonyl)ethyl)-Gly-OSu (46 mg) (prepared as described in WO 2005/012347) dissolved in acetonitrile/THF 1:1 (2.25 mL) was added. After stirring for 30 minutes at room temperature more tert-Butyl octadecandioyl-N-(2-(tert-butoxycarbonyl)ethyl)-Gly-OSu (46 mg) dissolved in acetonitrile/THF 1:1 (2.25 mL) was added. After 75 minutes water was added (5 mL) and pH was adjusted to 5.3 with 1N HCl. The precipitate was spinned down and lyophilised. The dry mixture wad treated with 0.1N NaOH at pH 12 on an ice bath for 45 min. pH was readjusted to 5.3 and the precipitate was spinned down and lyophilized. The solid was dissolved in ice-cold 95% trifluoroacetic acid (containing 5% water) and kept on ice for 45 minutes. The mixture was concentrated in vacuo and re-evaporated from dichloromethane. The residue was purified by RP-HPLC on a C18 column using A: 0.1% trifluoroacetic acid in water, buffer B: 0.1% trifluoroacetic acid in acetonitrile. Gradient 25% 1B to 70% B over 60 minutes. Product pools were partially evaporated in vacuo and freeze-dried providing A1N$^{\alpha}$-octadecandioyl-N-2-carboxyethyl-glycyl B29N$^{\epsilon}$-octadecandioyl-N-2-carboxyethyl-glycyl A14E B25H desB30 human insulin LCMS: 1628.7 Da [M+4H]$^{4+}$. Calculated for C$_{292}$H$_{450}$N$_{68}$O$_{88}$S$_6$ [M+4H]$^{4+}$: 1629.4 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 6511.1 Da, calculated for C$_{292}$H$_{450}$N$_{68}$O$_{88}$S$_6$. 6513.6 Da.

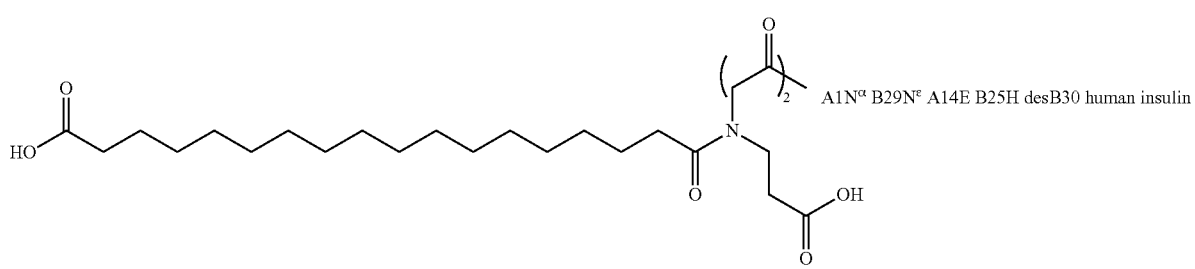

Example 19

A1N$^\alpha$-octadecandioyl-N-carboxymethyl-beta-alanyl A22N$^\epsilon$-N-octadecandioyl-N-carboxymethyl-beta-alanyl A22K B29R desB30 human insulin

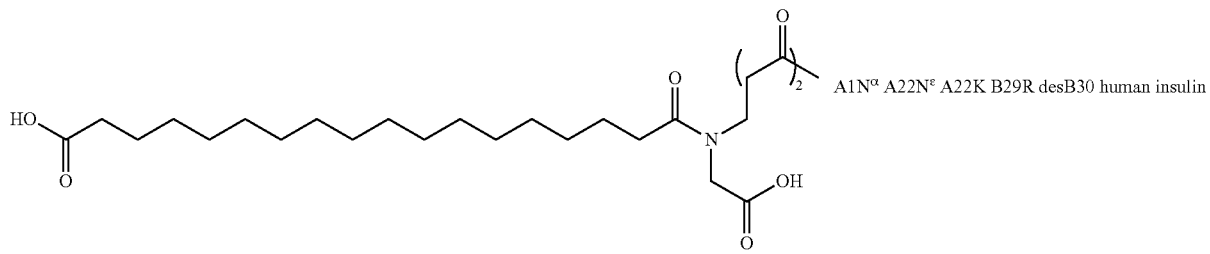

A22K B29R desB30 human insulin (200 mg) was dissolved in 100 mM aqueous Na$_2$CO$_3$ (4.5 mL), and pH adjusted to 10.1 with 1 N NaOH. tert-Butyl octadecandioyl-N-(tert-butoxycarbonylmethyl)-βAla-OSu (27 mg) (prepared as described in WO 2005/012347) was dissolved in acetonitrile/THF 1.2 (2.25 mL) and added to the insulin solution. Some precipitation was observed and more THF (1.0 mL) was added to give a clear solution. Ph was 10.7. After 57 minutes more tert-butyl octadecandioyl-N-(tert-butoxycarbonylmethyl)-βAla-OSu (14 mg) dissolved in THF (1.1 mL) was added. After 90 min, water (4.5 mL) was added and pH was adjusted to 5.5 with 1N HCl. The precipitate was spinned down and lyophilised. The solid was dissolved in ice-cold 95% trifluoroacetic acid (containing 5% water) and kept on ice for 25 minutes. The mixture was concentrated in vacuo. The residue was purified by RP-HPLC on a C18 column using A: 0.1% trifluoroacetic acid in water, buffer B: 0.1% trifluoroacetic acid in acetonitrile. Gradient 10% B to 55% B over 75 minutes. Product pools were partially evaporated in vacuo and freeze-dried providing A1N$^\alpha$-octadecandioyl-N-carboxymethylbeta-alanyl) A22N$^\epsilon$-octadecandioyl-N-carboxymethyl-beta-alanyl A22K B29R desB30 human insulin.

LCMS: 1679.0 Da [M+4H]$^{4+}$. Calculated for C$_{305}$H$_{466}$N$_{70}$O$_{88}$S$_6$ [M+4H]$^{4+}$: 1679.5 Da.

LCMS buffer A: 0.1% trifluoroacetic acid in water; buffer B: 0.1% trifluoroacetic acid in acetonitrile, gradient 10 to 90% B over 10 minutes.

MALDI: (matrix, HCCA); m/z: 6709.4 Da, calculated for C$_{305}$H$_{466}$N$_{70}$O$_{88}$S$_6$: 6713.9 Da.

Example 20

A22N$^\epsilon$-hexadecandioyl-γ-L-glutamyl-OEG-OEG B29N$^\epsilon$-hexadecandioyl-γ-L-glutamyl-OEG-OEG A14E B25H desB30 human insulin

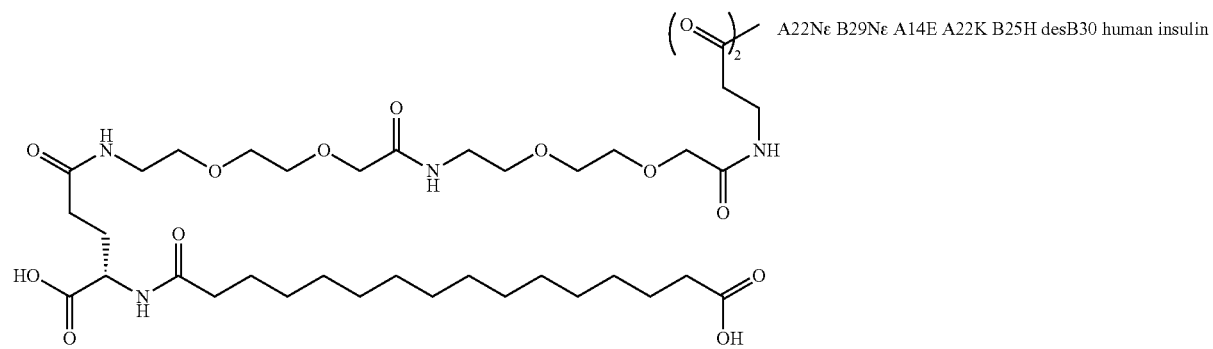

A14E A22K B25H desB30 human insulin (0.5 g, 86 μmol) was dissolved in 200 mM Na$_2$CO$_3$ (5 mL) and pH was adjusted to 11 with 1N NaOH. Then, hexadecandioyl-γ-L-glutamyl-OEG-OEG-succinimidyl (150 mg, 186 μmol) dissolved in NMP (0.5 mL) and acetonitrile (0.1 mL) were added to the insulin solution and 1N NaOH was added to keep pH at 11. The reaction was stirred for 5 minutes and the progress of reaction was monitored by LCMS. Octadecandioyl-γ-L-glutamyl-OEG-OEG-succinimidyl (150 mg, 186 μmol) dissolved in NMP (0.5 mL) and acetonitrile (0.1 mL) were added further 2 times (using the above protocol) before the target product was formed monitored by LCMS. The product was purified by RP-HPLC on C18 column using buffer A: 0.1% TFA in water, Buffer B: 0.1% TFA in acetonitrile and the gradient 25-50% acetonitrile over 60 minutes with a flow of 25 mL/min. The product was purified 2 times. Column: Phenomenex, Gemini, 5μ, C18, 110 Å, 250×30 cm. The pure fractions were then pooled and freeze dried.

LCMS: 1791.7 Da [M+4H]$^{4+}$. Calculated for C$_{318}$H$_{498}$N$_{74}$O$_{101}$S$_6$ [M+4H]$^{4+}$: 1790.5 Da.

LCMS buffer A: 0.1% trifluoroacetic acid in water; buffer B: 0.1% trifluoroacetic acid in acetonitrile, gradient 5 to 90% B over 4 minutes.

Example 21

A1N$^\alpha$-hexadecandioyl-γ-L-glutamyl-OEG-OEG
B29N$^\epsilon$-hexadecandioyl-γ-L-glutamyl-OEG-OEG
A14E B25H desB30 human insulin

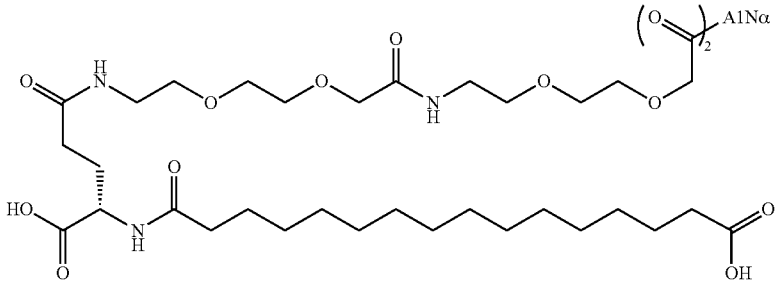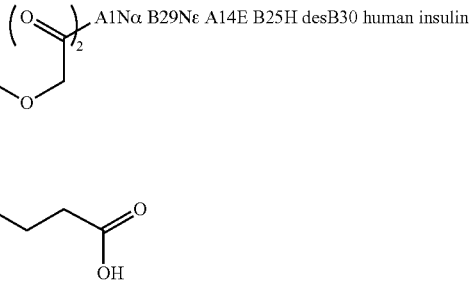

A14E B25H desB30 human insulin (500 mg, 88 μmol) was dissolved in 200 mM Na$_2$CO$_3$ (5 mL) and pH was adjusted to 11 with 1N NaOH. Then, hexadecandioyl-γ-L-glutamyl-OEG-OEG-succinimidyl (150 mg, 186 μmol) dissolved in NMP (0.5 mL) and acetonitrile (0.1 mL) were added to the insulin solution and 1N NaOH was added to keep pH at 11. The reaction was stirred for 5 minutes and the progress of reaction was monitored by LCMS. The linker, hexadecandioyl-γ-L-glutamyl-OEG-OEG-succinimidyl (150 mg, 186 μmol) dissolved in NMP (0.5 mL) and acetonitrile (0.1 mL) were added further 3 times (using the above protocol) before the target product was the major product monitored by LCMS. The product was purified by RP-HPLC on C18 column using buffer A: 0.1% TFA in water, Buffer B: 0.1% TFA in acetonitrile and the gradient 30-45% acetonitrile over 60 minutes with a flow of 25 mL/min. Column: Phenomenex, Gemini, 5μ, C18, 110 Å, 250×30 cm. The product was purified 2 times. The pure fractions were then pooled and freeze dried.

LCMS: 1760.3 Da [M+4H]$^{4+}$. Calculated for C$_{312}$H$_{486}$N$_{72}$O$_{100}$S$_6$ [M+4H]$^{4+}$: 1758.5 Da.

LCMS buffer A: 0.1% trifluoroacetic acid in water; buffer B: 0.1% trifluoroacetic acid in acetonitrile, gradient 5 to 90% B over 4 minutes.

Example 22

A1N$^\alpha$-hexadecandioyl-γ-L-glutamyl-OEG-OEG
B29N$^\epsilon$-hexadecandioyl-γ-L-glutamyl-OEG-OEG
A14E B16H B25H desB30 human insulin A14E B16H B25H, desB30 human insulin (1 g, 177 μmol) was dissolved in 200 mM Na2CO3 (12.5 mL) and pH was adjusted to 11 with addition of 1N NaOH. Then, hexadecandioyl-γ-L-glutamyl-OEG-OEG-succinimidyl (400 mg, 499 μmol) dissolved in NMP (1.0 mL) and acetonitrile (0.2 mL) were added to the insulin solution over 10 min. 1N NaOH was added additional to keep pH at 11.0 during the reaction. The reaction mixture was stirred for 30 minutes at room temperature and progress of reaction was monitored by LCMS and the product was purified by RP-HPLC on C18 column using buffer A: 0.1% TFA in water, Buffer B: 0.1% TFA in acetonitrile and the gradient 25-40% acetonitrile over 60 minutes with a flow of 25 mL/min. The pure fractions were then pooled and freeze dried.

LCMS: 1402.9 Da [M+5H]$^{5+}$. Calculated for C$_{309}$H$_{484}$N$_{74}$O$_{99}$S$_6$ [M+5H]$^{5+}$: 1403.0 Da.

LCMS buffer A: 0.1% trifluoroacetic acid in water; buffer B: 0.1% trifluoroacetic acid in acetonitrile, gradient 5 to 90% B over 4 minutes.

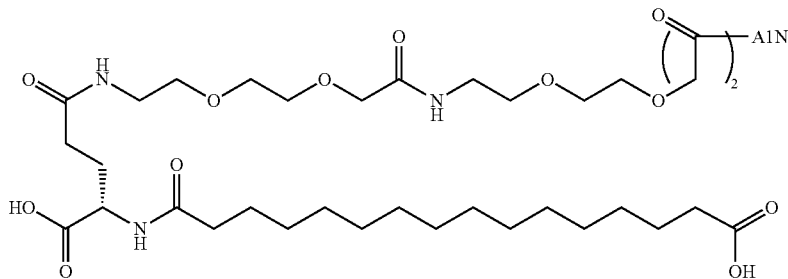

Example 23

A1N$^\alpha$-octadecandioyl-γ-L-glutamyl-OEG-OEG
B1N$^\alpha$-octadecandioyl-γ-L-glutamyl-OEG-OEG
A14E B25H B29R desB30 human insulin

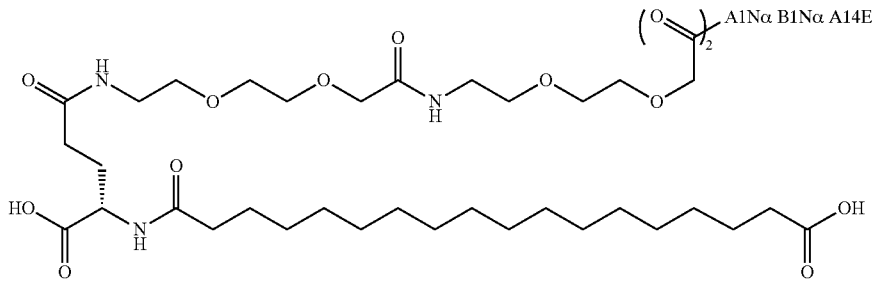

A14E B25H B29R desB30 human insulin (0.35 g, 61 μmol) was dissolved in H2O (3 mL) and pH was adjusted to 11. Then, octadecandioyl-γ-L-glutamyl-OEG-OEG-succinimidyl (100 mg, 120 μmol) dissolved in NMP (0.4 mL) and acetonitrile (0.1 mL) were added to the insulin solution and 1N NaOH was added to keep pH at 11. The reaction was stirred for 5 minutes and the progress of reaction was monitored by LCMS. Octadecandioyl-γ-L-glutamyl-OEG-OEG-succinimidyl (150 mg, 120 μmol) dissolved in NMP (0.4 mL) and acetonitrile (0.1 mL) were added further and the progress of the formed major product was monitored by LCMS. The product was purified 2 times by RP-HPLC on C18 column using buffer A: 0.1% TFA in water, Buffer B: 0.1% TFA in acetonitrile and the gradients; 30-45% acetonitrile over 60 minutes and 10-40% acetonitrile over 60 minutes with a flow of 25 mL/min. The pure fractions were then pooled and freeze dried.

LCMS: 1189.9.88 Da [M+6H]$^{6+}$. Calculated for $C_{316}H_{494}N_{74}O_{100}S_6$ [M+6H]$^{6+}$: 1188 Da.

LCMS buffer A: 0.1% trifluoroacetic acid in water; buffer B: 0.1% trifluoroacetic acid in acetonitrile, gradient 5 to 90% B over 4 minutes.

Example 24

A22N$^\epsilon$-eicosandioyl-γ-L-glutamyl-OEG-OEG
B29N$^\epsilon$-eicosandioyl-γ-L-glutamyl-OEG-OEG A14E
A22K B25H desB30 human insulin A14E A22K B25H desB30 human insulin (450 mg, 77 μmol) was dissolved in 200 mM Na$_2$CO$_3$ (5 mL) and pH was adjusted to 11 with 1N NaOH. Then, eicosandioyl-γ-L-glutamyl-OEG-OEG-succinimidyl (150 mg, 174 μmol) dissolved in NMP (0.5 mL) and acetonitrile (0.1 mL) were added to the insulin solution and 1N NaOH was added to keep pH at 11. The reaction was stirred for 5 min. Then, the progress of reaction was monitored by LCMS Eicosandioyl-γ-L-glutamyl-OEG-OEG-succinimidyl (150 mg, 174 μmol) dissolved in NMP (0.5 mL) and acetonitrile (0.1 mL) was added further 2 times (using the above protocol) before the target product was formed monitored by LCMS. The product was purified 2 times by RP-HPLC on C18 column using 1) buffer A: 0.1% TFA in water, Buffer B: 0.1% TFA in acetonitrile and the gradient; 25-50% acetonitrile over 40 minutes with a flow of 25 mL/min 2) buffer A: 10 mM Tris, 15 mM ammonium sulfate, pH 7.3 in water/acetonitrile 80/20, buffer B: water/acetonitrile 20/80 and the gradient; 10-60% buffer B over 60 minutes with a flow of 25 mL/min. The pure fractions were then pooled and freeze dried.

LCMS: 1820.1 Da [M+4H]$^{4+}$. Calculated for $C_{326}H_{514}N_{74}O_{101}S_6$ [M+4H]$^{4+}$: 1820.5 Da.

LCMS buffer A: 0.1% trifluoroacetic acid in water; buffer B: 0.1% trifluoroacetic acid in acetonitrile, gradient 5 to 90% B over 4 minutes.

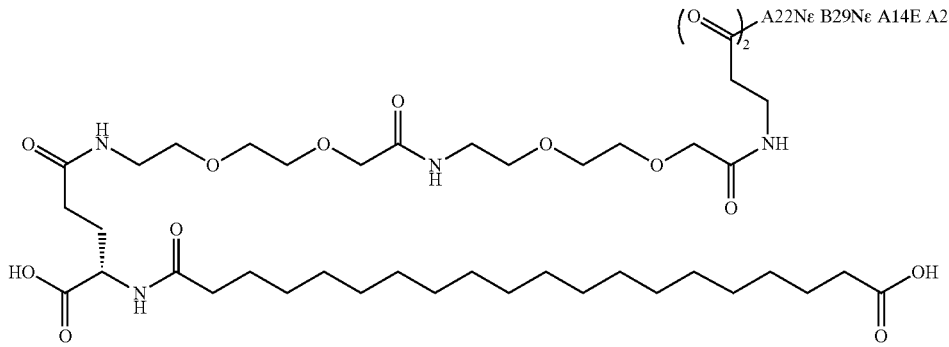

Example 25

B1Nα-octadecandioyl-γ-L-glutamyl-OEG-OEG-4-aminomethyl-benzyl B29Nε-octadecandioyl-γ-L-glutamyl-OEG-OEG A14E B16H B25H desB30 human insulin LCMS: 1438.3 Da $[M+5H]^{5+}$. Calculated for $C_{321}H_{501}N_{75}O_{99}S_6$ $[M+5H]^{5+}$: 1438.4 Da.

LCMS buffer A: 0.1% trifluoroacetic acid in water; buffer B: 0.1% trifluoroacetic acid in acetonitrile, gradient 5 to 90% B over 4 minutes. Amino acid sequencing of the peptide verified that C18diacid-γ-LGlu-OEG-OEG-aminomethyl-benzyl was attached to B1 (alkylation).

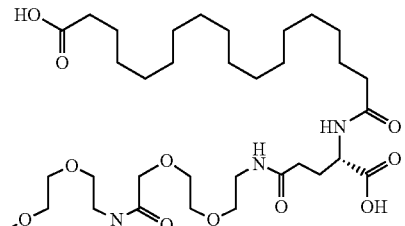

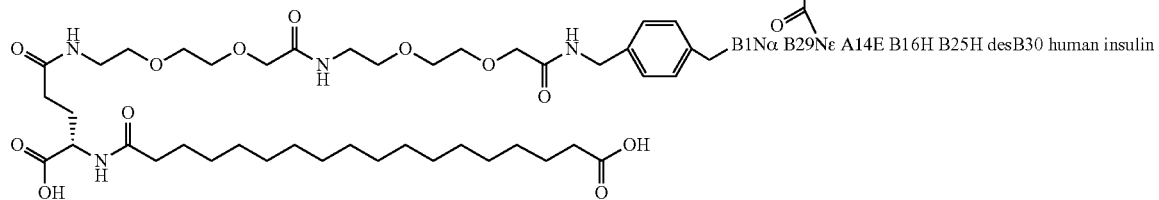

Octadecandioyl-γ-L-glutamyl-OEG-OEG-4-aminomethyl-benzaldehyde (100 mg, 117 µmol) was dissolved in 2 mL 25 mM HEPES (2 mL) by heating (tap water) and 20% HPCD (500 µL) was then added to give a unclear but homogeneous solution. To B29Nε-octadecandioyl-γ-L-glutamyl-OEG-OEG A14E B16H B25H desB30 human insulin (250 mg, 39.8 µmol) was added 25 mM HEPES (5 mL, pH 5.6) and pH was adjusted to 5.0 with 1 N HCl. The above aldehyde solution (2.5 mL) was added to insulin and the solution became unclear. After 5 min, 1M NaCNBH₃ in MeOH (165 µL) was added and the progress of the reaction was monitored both by LCMS and UPLC.

The product was purified by RP-HPLC on C18 column using buffer A: 0.1% TFA in water, Buffer B: 0.1% TFA in acetonitrile and the gradient; 30-55% acetonitrile over 40 minutes with a flow of 25 mL/min. The pure fractions were then pooled and freeze dried.

Example 26

B1Nα-octadecandioyl-γ-L-glutamyl-OEG-OEG-4-aminomethyl-benzyl B29Nε-octadecandioyl-γ-L-glutamyl-OEG-OEG A14E B25H desB30 human insulin

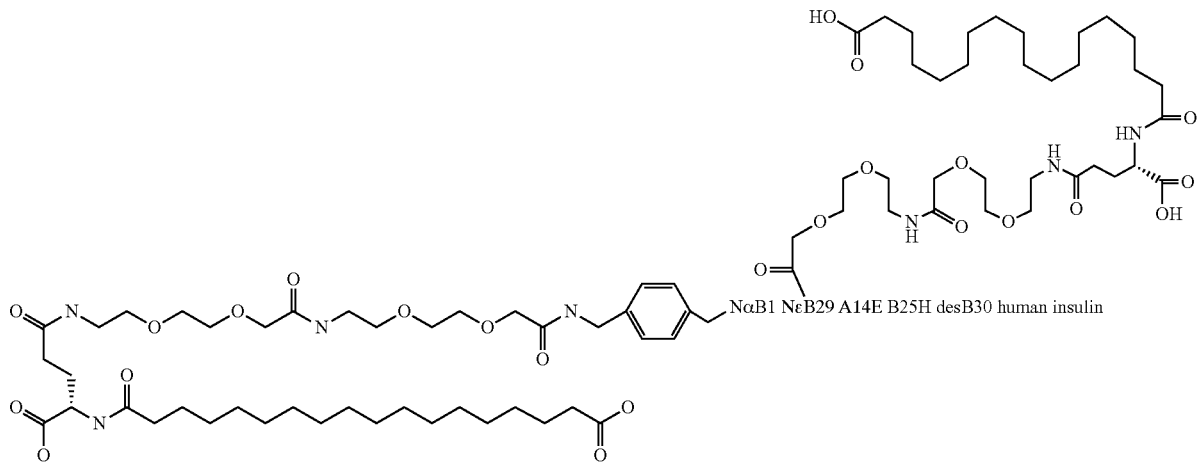

Octadecandioyl-γ-L-glutamyl-OEG-OEG-4-aminomethyl-benzaldehyde (100 mg, 117 mmol) was dissolved in 25 mM HEPES (2 mL) by heating (tap water). 20% HPCD (500 µL) was then added to give a unclear but homogeneous solution.

To B29N$^e$-octadecandioyl-γ-L-glutamyl-OEG-OEG A14E B25H desB30 human insulin (250 mg, 39 μmol) was added 25 mM HEPES (5 mL, pH 5.6) and pH was adjusted to 5.0 with 1 N HCl). The aldehyde solution (2.5 mL) was added to insulin and the solution became unclear. After 5 minutes, 1M NaCNBH$_3$ in MeOH (165 μL) was added. The progress of the reaction was monitored both by LCMS and uplc. The product was purified by RP-HPLC on C18 column using buffer A: 0.1% TFA in water, Buffer B: 0.1% TFA in acetonitrile and the gradient; 30-55% acetonitrile over 40 minutes with a flow of 25 mL/min. Kolonne: Phenomenex, Gemini, 5μ, C18, 110 Å, 250×30 cm. The pure fractions were then pooled and freeze dried.

LCMS: 1802.4 Da [M+4H]$^{4+}$. Calculated for C$_{324}$H$_{503}$N$_{73}$O$_{100}$S$_6$ [M+4H]$^{4+}$: 1804 Da.

LCMS buffer A: 0.1% trifluoroacetic acid in water; buffer B: 0.1% trifluoroacetic acid in acetonitrile, gradient 5 to 90% B over 4 minutes. Amino acid sequencing of the peptide verified that C18diacid-γ-LGlu-OEG-OEG-4-aminomethyl-benzyl was attached to B1 (alkylation).

Example 27

B1N$^α$-octadecandioyl-γ-L-glutamyl-OEG-OEG-4-aminomethyl-benzyl B29N$^ε$-octadecandioyl-γ-L-glutamyl-OEG-OEG A14E B25H desB27 desB30 human insulin To B29N$^ε$-octadecandioyl-γ-L-glutamyl-OEG-OEG A14E B25H desB27 desB30 human insulin (350 mg, 55 μmol) was added 25 mM HEPES (7 mL, pH 5.6) and pH was adjusted to 5.5 with 1 N HCl. Aldehyde solution (3.5 mL) was added and the solution was unclear. A few minutes later 1M NaCNBH$_3$ in MeOH (230 μL) was added. After 30 minutes was the progress of the reaction monitored by LCMS and the desired product was then formed. 1N HCl was added to acidified the reaction mixture before preparative HPLC purification. The product was purified by RP-HPLC on C18 column using buffer A: 0.1% TFA in water, Buffer B: 0.1% TFA in acetonitrile and the gradient; 25-65% acetonitrile over 40 minutes with a flow of 25 mL/min. The pure fractions were then pooled and freeze dried.

LCMS: 1423.4 Da [M+5H]$^{5+}$. Calculated for C$_{320}$H$_{496}$N$_{72}$O$_{98}$S$_6$ [M+5H]$^{5+}$: 1423.5 Da.

LCMS buffer A: 0.1% trifluoroacetic acid in water; buffer B: 0.1% trifluoroacetic acid in acetonitrile, gradient 5 to 90% B over 4 minutes. Amino acid sequencing of the peptide verified that C18diacid-γ-LGlu-OEG-OEG-4-aminomethyl-benzyl was attached to B1 (alkylation).

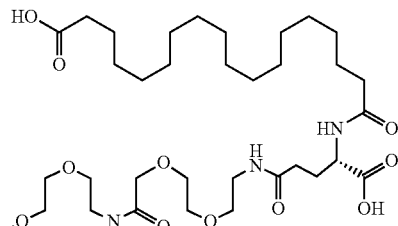

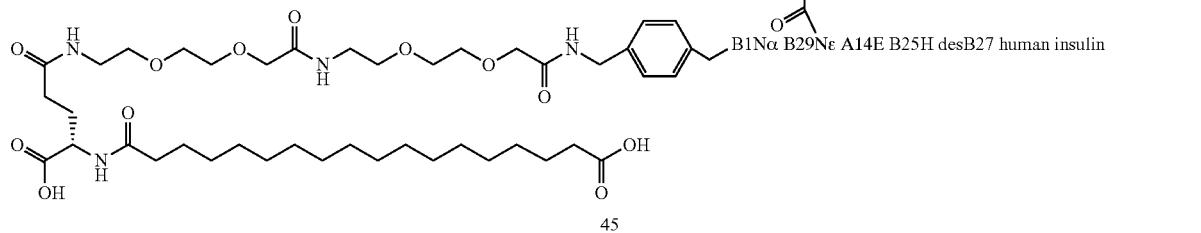

Octadecandioyl-γ-L-glutamyl-OEG-OEG-4-aminomethyl-benzaldehyde (140 mg, 163 μmol) was dissolved in 25 mM HEPES (2.8 mL) by heating (tap water). 20% HPCD (700 μL) was added to give a solution which was unclear but homogeneous.

Example 28

A22N$^ε$-4-carboxyphenoxy-decanoyl-γ-L-glutamyl-OEG-OEG B29N$^ε$-4-carboxyphenoxy-decanoyl-γ-L-glutamyl-OEG-OEG A14E A22K B25H desB30 human insulin

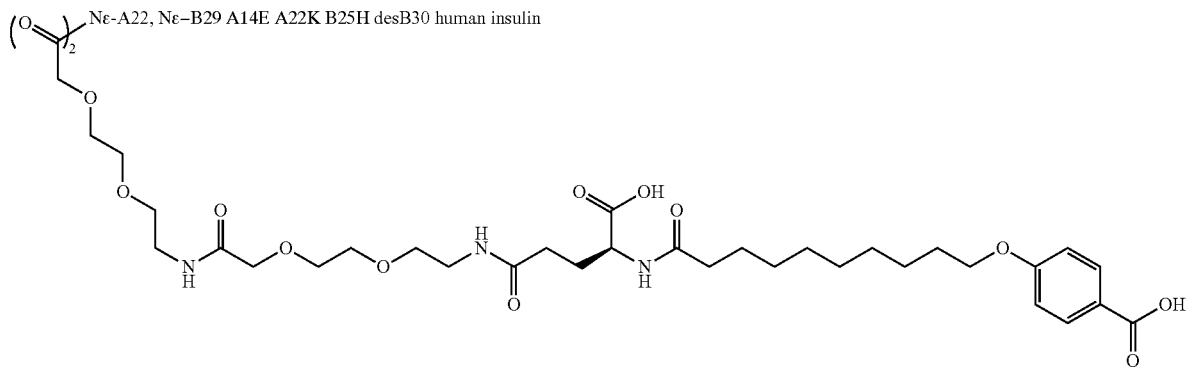

This compound was prepared in analogy with the compound of example 4 by using 4-tert-butyl-carboxyphenoxy-decanoyl-γ-L-glutamyl-α-tert-butyl-OEG-OEG-succinimidyl (prepared in analogue with the description in WO06082204) and A14E B25H A22K desB30 human insulin.

Product LCMS: 1806.5 Da $[M+4H]^{4+}$.

Calculated for $C_{320}H_{486}N_{74}O_{103}S_6$ $[M+4H]^{4+}$: 1803.6 Da.

Example 29

Human Insulin Receptor Affinity, Albumin Affinity, Mean Residence Time for Insulin Derivatives According to the Present Invention Data in table 1 is presented for insulin derivatives according to the present invention (di- and trisubstituted insulins) and one monosubstituted insulin. The affinity of the acylated insulin analogues of this invention for the human insulin receptor was determined by a SPA assay (Scintillation Proximity Assay) microtiterplate antibody capture assay. Anaesthetized rats are dosed intravenously (i.v.) with insulin analogues at various doses and plasma concentrations of the employed compounds are measured using immunoassays or mass spectrometry at specified intervals for 4 hours or more post-dose. Pharmacokinetic parameters where subsequently calculated using WinNonLin Professional (Pharsight Inc., Mountain View, Calif., USA).

A. Human insulin receptor affinity, dissociation constants (Kd) for insulin derivative examples binding to human insulin receptor isoform A (hIRA) relative to the value for human insulin.

B. Prolongation in vivo measured as mean residence time (MRT) upon intravenous administration of insulin derivative examples to rats.

C. B29N$^\epsilon$hexadecandioylγ-L-glutamyl desB30 human insulin is designated "C" in this list and represents a monosubstituted reference for comparison of values only.

TABLE 1

| Example number | A: Affinity for hIRA, Kd (relative %) | B: MRT i.v. rats (h) |
|---|---|---|
| Monosubstituted insulin* | | |
| C | 18.3 | 1.8 |
| Insulin derivative according to the present invention | | |
| 1 | 16.1 | N/A |
| 2 | 6.5 | 6.4 |

TABLE 1-continued

| Example number | A: Affinity for hIRA, Kd (relative %) | B: MRT i.v. rats (h) |
|---|---|---|
| 3 | 36.9 | N/A |
| 4 | 7.9 | 9.0 |
| 5 | 3.1 | 10.0 |
| 6 | 1.4 | 10.3 |
| 7 | N/A | 12.0 |
| 8 | 0.4 | 5.0 |
| 9 | 0.1 | 19.5 |
| 10 | 12.3 | 20.0 |
| 11 | 7.5 | 17.0 |
| 12 | 16.1 | 13.0 |
| 13 | N/A | 3.4 |
| 14 | N/A | N/A |
| 15 | 2.6 | 22.0 |
| 16 | 0.5 | N/A |
| 17 | N/A | N/A |
| 18 | N/A | N/A |
| 19 | N/A | N/A |
| 20 | 3.1 | 11.5 |
| 21 | 0.2 | 13.0 |
| 22 | 0.04 | 20.0 |
| 23 | 1.2 | 21.0 |
| 24 | 0.3 | 11.0 |
| 25 | 0.8 | 27.0 |
| 26 | 2.1 | 21.0 |
| 27 | 2.1 | 31.0 |
| 28 | 5.6 | 5.3 |
| 26 | 2.1 | 21.0 |
| 27 | 2.1 | 31.0 |
| 28 | 5.6 | 5.3 |
| 30 | 0.04 | 26 |
| 31 | 0.15 | N/A |
| 32 | 3.26 | N/A |
| 33 | 0.57 | N/A |
| 34 | 14.5 | 17 |
| 35 | 11.4 | N/A |

While certain features of the invention have been illustrated and described herein, many modifications, substitutions, changes, and equivalents will now occur to those of ordinary skill in the art. It is, therefore, to be understood that the appended aspects are intended to cover all such modifications and changes as fall within the true spirit of the invention.

Example 30

A1N$^\alpha$-octadecandioyl-gamma-L-glutamyl-OEG-OEG B29N$^\epsilon$-octadecandioyl-gamma-L-glutamyl-OEG-OEG A14E B16H B25H desB30 human insulin

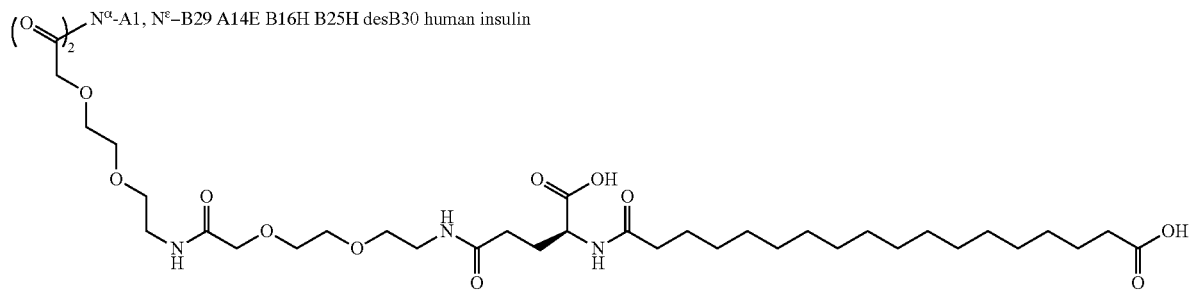

This compound was prepared in analogy with the compound of example 7 by using octadecandioyl-γ-L-glutamyl-OEG-OEG-succinimidyl and A14E B16H B25H desB30 human insulin.

Product LCMS: 1767.9 Da [M+4H]$^{4+}$.
Calculated for $C_{313}H_{492}N_{74}O_{99}S_6$ [M+4H]$^{4+}$: 1768.1 Da.

Example 31

A1N$^{\alpha}$-octadecandioyl-gamma-L-glutamyl-OEG-OEG B29N$^{\epsilon}$-octadecandioyl-gamma-L-glutamyl-OEG-OEG A14E B16H desB27 desB30 human insulin

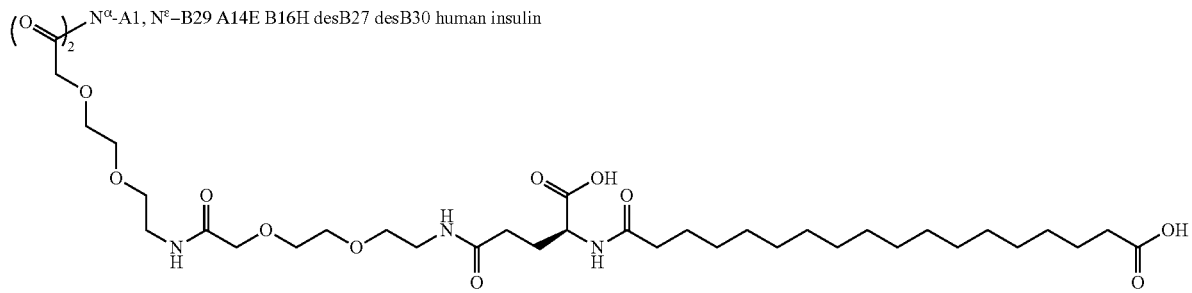

This compound was prepared in analogy with the compound of example 7 by using octadecandioyl-γ-L-glutamyl-OEG-OEG-succinimidyl and A14E B16HdesB27 desB30 human insulin.

Product LCMS: 1744.8 Da [M+4H]$^{4+}$.
Calculated for $C_{312}H_{487}N_{71}O_{97}S_6$ [M+4H]$^{4+}$: 1745.3 Da.

Example 32

B1N$^{\alpha}$-octadecandioyl-γ-L-glutamyl-OEG-OEG-4-aminomethyl-benzyl B29N$^{\epsilon}$-octadecandioyl-γ-L-glutamyl-OEG-OEG-4-aminomethyl-benzyl A14E B25H desB30 human insulin To a suspension of A14E B25H desB30 human insulin (50 mg) in DMSO (1.5 ml) was added a solution of octadecandioyl-γ-L-glutamyl-OEG-OEG-4-aminomethyl-benzaldehyde (11.3 mg) in DMSO (0.5 mL). After 20 min, the mixture was clear and a 1 M 2-picoline borane complex in DMSO (0.041 ml) was added. After 2.5 h and after 21 h additional 1 M 2-picoline borane complex in DMSO (0.041 ml) was added. The mixture was purified after 24.5 h by RP-HPLC on a C18 column using A: 0.1% trifluoroacetic acid in water, buffer B: 0.1% trifluoroacetic acid in acetonitrile. Gradient 20% B to 60% B over 60 minutes. Product pools were partially evaporated in vacuo and freeze-dried providing B1N$^{\alpha}$-octadecandioyl-γ-L-glutamyl-OEG-OEG-4-aminomethyl-benzyl B29N$^{\epsilon}$-octadecandioyl-γ-L-glutamyl-OEG-OEG-4-aminomethyl-benzyl A14E B25H desB30 human insulin LCMS: 1833.81 Da [M+4H]$^{4+}$. Calculated for $C_{332}H_{512}N_{74}O_{100}S_6$ [M+4H]$^{4+}$: 1834.15 Da.

MALDI: (matrix, HCCA); m/z: 7332.76 Da, calculated: 7332.60 Da

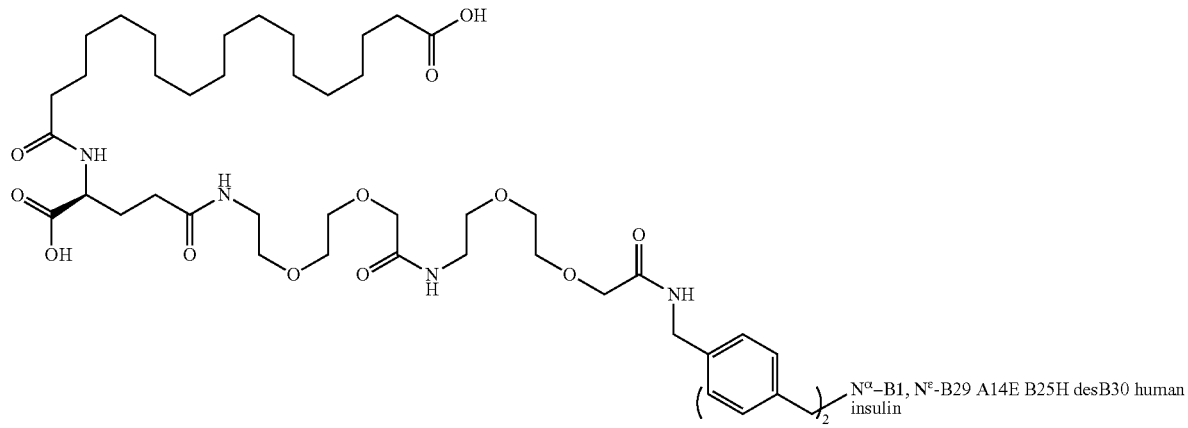

Example 33

A1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin This compound was prepared in analogy with the compound of example 27 by using octadecandioyl-γ-L-glutamyl-OEG-OEG-4-aminomethyl-benzaldehyde and octadecandioyl-γ-L-glutamyl-OEG-OEG-succinimidyl and A14E desB27 desB30 human insulin.

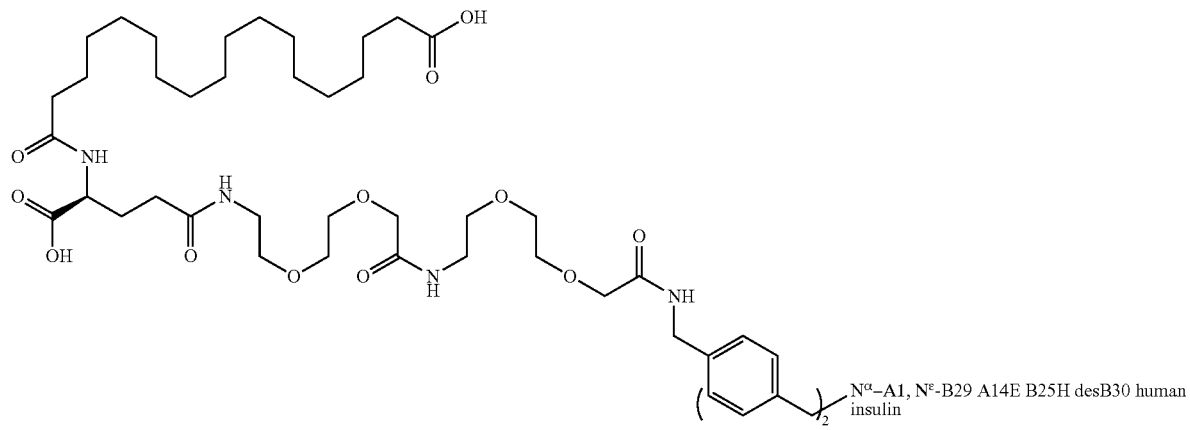

A1N$^\alpha$-octadecandioyl-γ-L-glutamyl-OEG-OEG-4-aminomethyl-benzyl B29N$^\epsilon$-octadecandioyl-γ-L-glutamyl-OEG-OEG-4-aminomethyl-benzyl A14E B25H desB30 human insulin was isolated from the reaction mixture described in example 32.

LCMS: 1834.14 Da [M+4H]$^{4+}$. Calculated for $C_{332}H_{512}N_{74}O_{100}S_6$ [M+4H]$^{4+}$: 1834.15 Da.

MALDI: (matrix, HCCA); m/z: 7332.94 Da, calculated: 7332.60 Da

Product LCMS: 1781.8 Da [M+4H]$^{4+}$.

Calculated for $C_{323}H_{498}N_{70}O_{98}S_6$ [M+4H]$^{4+}$: 1781.6 Da.

Example 34

B1N$^\alpha$-octadecandioyl-γ-L-glutamyl-OEG-OEG-4-aminomethyl-benzyl B29N$^\epsilon$-octadecandioyl-γ-L-glutamyl-OEG-OEG A14E desB27 desB30 human insulin

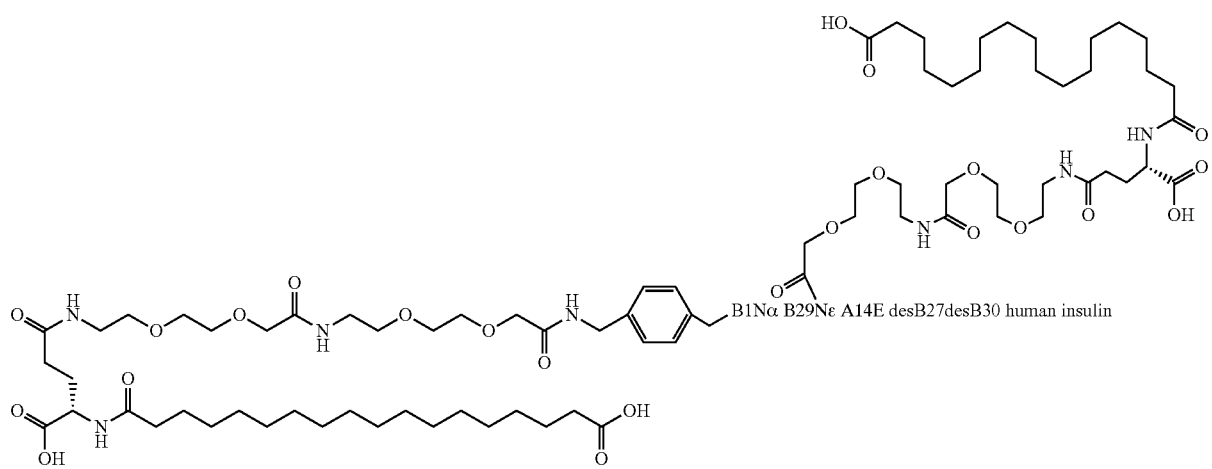

Example 35

B1N$^α$-octadecandioyl-γ-L-glutamyl-OEG-OEG-OEG-OEG-4-aminomethyl-benzyl B29N$^ε$-octadecandioyl-γ-L-glutamyl-OEG-OEG-OEG-OEG A14E desB27 desB30 human insulin

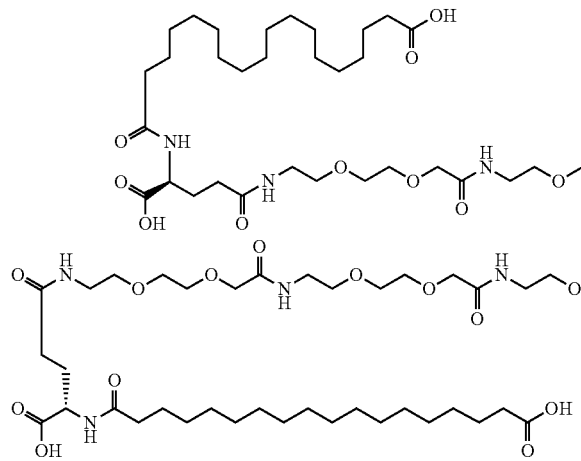

This compound was prepared in analogy with the compound of example 27 by using octadecandioyl-γ-L-glutamyl-OEG-OEG-OEG-OEG-4-aminomethyl-benzaldehyde and octadecandioyl-γ-L-glutamyl-OEG-OEG-OEG-OEG-succinimidyl and A14E desB27 desB30 human insulin.

Product LCMS: 1926.8Da [M+4H]$^{4+}$.

Calculated for $C_{347}H_{542}N_{74}O_{110}S_6$ [M+4H]$^{4+}$: 1926.8 Da.

The invention claimed is:

1. A soluble insulin derivative or pharmaceutically acceptable salt thereof selected from the group consisting of A1N$^α$-octadecandioyl-γ-L-glutamyl-OEG-OEG-aminomethyl-benzyl B1N$^α$-octadecandioyl-γ-L-glutamyl-OEG-OEG-4-aminomethyl-benzyl A14E B25H desB27 desB30 human insulin, A1N$^α$-octadecandioyl-γ-L-glutamyl-OEG-OEG-aminomethyl-benzyl B1N$^α$-octadecandioyl-γ-L-glutamyl-OEG-OEG-4-aminomethyl-benzyl A14E B25H desB30 human insulin, A1N$^α$-hexadecandioyl-γ-L-glutamyl-OEG-OEG-aminomethyl-benzyl B1N$^α$-hexadecandioyl-γ-L-glutamyl-OEG-OEG-4-aminomethyl-benzyl A14E B25H desB27 desB30 human insulin, A1N$^α$-tetradecandioyl-γ-L-glutamyl-OEG-OEG-aminomethyl-benzyl B1N$^α$-tetradecandioyl-γ-L-glutamyl-OEG-OEG-4-aminomethyl-benzyl A14E B25H desB27 desB30 human insulin, A1N$^α$-hexadecandioyl-γ-L-glutamyl-OEG-OEG-4-aminomethyl-benzyl B1N$^α$-hexadecandioyl-γ-L-glutamyl-OEG-OEG-4-aminomethyl-benzyl A14E B25H desB30 human insulin, B1N-octadecandioyl-γ-L-glutamyl-OEG-OEG-aminomethyl-benzyl B29N$^ε$-octadecandioyl-γ-L-glutamyl-OEG-OEG A14E B25H desB30 human insulin, A1N$^α$-octadecandioyl-γ-L-glutamyl-OEG-OEG-4-aminomethyl-benzyl B1N$^α$-octadecandioyl-γ-L-glutamyl-OEG-OEG-4-aminomethyl-benzyl B29N$^ε$-octadecandioyl-γ-L-glutamyl-OEG-OEG A14E B25H desB30 human insulin, B1N$^α$-octadecandioyl-γ-L-glutamyl-OEG-OEG-4-aminomethyl-benzyl B29N$^ε$-octadecandioyl-γ-L-glutamyl-OEG-OEG A14E B16H B25H desB30 human insulin, B1N$^α$-octadecandioyl-γ-L-glutamyl-OEG-OEG-4-aminomethyl-benzyl A14E B25H B29N$^ε$-octadecandioyl-γ-L-glutamyl-OEG-OEG desB30 human insulin, and B1N$^α$-octadecandioyl-γ-L-glutamyl-OEG-OEG-aminomethyl-benzyl B29N$^ε$-octadecandioyl-γ-L-glutamyl-OEG-OEG A14E B25H desB27 desB30 human insulin, wherein OEG is *—NH—(CH$_2$)$_2$O—(CH$_2$)$_2$O—CH$_2$CO—*.

2. A soluble insulin derivative or a pharmaceutically acceptable salt thereof of general formula XZ$_n$-Ins-Z$^1_m$X$^1$, wherein Ins represents an insulin comprising a B29 lysine or B29 arginine residue and/or a A22 lysine residue, X is a fatty diacid substitution, X$^1$ is a fatty diacid substitution, Z is a linker between X and Ins, Z$^1$ is a linker between Ins and X$^1$, n is zero or 1, and m is zero or 1, and wherein at least one of Z and Z$^1$ comprises OEG-OEG-aminomethyl-benzyl, wherein OEG is *—NH—(CH$_2$)$_2$O—(CH$_2$)$_2$O—CH$_2$CO—*.

3. The soluble insulin derivative or a pharmaceutically acceptable salt thereof according to claim 2, wherein Ins represents an insulin comprising a B29 lysine or B29 arginine residue and a A22 lysine residue, and X is located at said A22 lysine residue.

4. The soluble insulin derivative or a pharmaceutically acceptable salt thereof according to claim 3, wherein said fatty diacid substitutions each comprise 14-20 carbon atoms.

5. The soluble insulin derivative or a pharmaceutically acceptable salt thereof according to claim 4, wherein X$^1$ is located at a position selected from the group consisting of B29 lysine, N-terminus of the A chain, and N-terminus of the B chain.

6. The soluble insulin derivative or a pharmaceutically acceptable salt thereof according to claim 4, wherein X$^1$ is located at a position selected from the group consisting of N-terminus of the A chain, and N-terminus of the B chain.

7. The soluble insulin derivative or a pharmaceutically acceptable salt thereof according to claim 4, wherein X$^1$ is located at a position selected from the group consisting of B29 lysine and N-terminus of the B chain.

8. The soluble insulin derivative or pharmaceutically acceptable salt thereof according to claim 3, wherein said fatty acid substitutions are each selected from a group of protracting moieties selected from Chem. 3 and Chem. 4, wherein Chem 3 is HOOC—$(CH_2)_x$—CO—*, and Chem 4 is HOOC—$C_6H4$-O—$(CH_2)_y$—CO—*, wherein x is an integer from 10 to 20 and y is an integer from 6 to 14.

9. The soluble insulin derivative or pharmaceutically acceptable salt thereof according to claim 8, wherein x is 14, 16 or 18 and y is 8, 10 or 12.

10. The soluble insulin derivative or pharmaceutically acceptable salt thereof according to claim 5, wherein said fatty acid substitutions are each selected from a group of protracting moieties selected from Chem. 3 and Chem. 4, wherein Chem 3 is HOOC—$(CH_2)$x-CO—*, and Chem 4 is HOOC—$C_6H4$-O—$(CH_2)$y-CO—*, wherein x is 14, 16 or 18 and y is 8, 10 or 12.

11. The soluble insulin derivative or pharmaceutically acceptable salt thereof according to claim 10, wherein Z and $Z^1$ comprise one or more linker elements selected from the group consisting of selected from the group consisting of: alpha-L-Glu, alpha-D-Glu, gamma-L-Glu, gamma-D-Glu, alpha-L-Asp, alpha-D-Asp, beta-L-Asp, beta-D-Asp, CPH, IDA and OEG, wherein CPH is *—$CH_2PhCH_2NH$—*, IDA is *—$N((CH_2)_nCOOH)(CH_2)_mCO$—*, wherein n is 1 or 2 and m is 1 or 2, and OEG is *—NH—$(CH_2)_2O$—$(CH_2)_2O$—$CH_2CO$—*, wherein at least one of Z and $Z^1$ comprises OEG-OEG-aminomethyl-benzyl.

12. A pharmaceutical composition comprising a soluble insulin derivative or a pharmaceutically acceptable salt thereof of claim 2 and a pharmaceutically suitable excipient.

13. A pharmaceutical composition comprising a soluble insulin derivative or a pharmaceutically acceptable salt thereof of claim 1 and a pharmaceutically suitable excipient.

14. A method of treating hyperglycemia, type 2 diabetes, impaired glucose tolerance, or type 1 diabetes in a subject in need of said treatment, said method comprising administering to a said subject a therapeutically effective amount of a pharmaceutical composition of claim 12.

15. A method of treating hyperglycemia, type 2 diabetes, impaired glucose tolerance, or type 1 diabetes in a subject in need of said treatment, said method comprising administering to a said subject a therapeutically effective amount of a pharmaceutical composition of claim 13.

* * * * *

UNITED STATES PATENT AND TRADEMARK OFFICE
CERTIFICATE OF CORRECTION

| | | |
|---|---|---|
| PATENT NO. | : 9,260,503 B2 | Page 1 of 1 |
| APPLICATION NO. | : 14/126215 | |
| DATED | : February 16, 2016 | |
| INVENTOR(S) | : Hoeg-Jensen et al. | |

It is certified that error appears in the above-identified patent and that said Letters Patent is hereby corrected as shown below:

In the Claims:

Column 76, claim 11, line 1, should read:

"... group consisting of:..."

Signed and Sealed this
Third Day of May, 2016

Michelle K. Lee
*Director of the United States Patent and Trademark Office*